(12) United States Patent
Liu et al.

(10) Patent No.: US 11,957,758 B2
(45) Date of Patent: Apr. 16, 2024

(54) PHARMACEUTICAL COMPOSITION OF DOCETAXEL CONJUGATE AND PREPARATION METHOD

(71) Applicants: SHENZHEN SALUBRIS PHARMACEUTICALS CO. LTD, Guangdong (CN); Ningbo Combireg Pharmaceutical Technology Co., Ltd, Ningbo (CN)

(72) Inventors: Gang Liu, Guangdong (CN); Xuan Zhang, Guangdong (CN); Wenming Cheng, Guangdong (CN); Shuo Li, Guangdong (CN); Xiaoming Wen, Guangdong (CN); Qianli Zhang, Guangdong (CN)

(73) Assignees: Shenzhen Salubris Pharmaceuticals Co. Ltd., Guangdong (CN); Ningbo Combireg Pharmaceutical Technology Co., Ltd., Zhejiang Province (CN)

( * ) Notice: Subject to any disclaimer, the term of this patent is extended or adjusted under 35 U.S.C. 154(b) by 355 days.

(21) Appl. No.: 16/645,047

(22) PCT Filed: Sep. 4, 2018

(86) PCT No.: PCT/CN2018/103887
§ 371 (c)(1),
(2) Date: Mar. 6, 2020

(87) PCT Pub. No.: WO2019/047812
PCT Pub. Date: Mar. 14, 2019

(65) Prior Publication Data
US 2020/0282064 A1 Sep. 10, 2020

(30) Foreign Application Priority Data
Sep. 7, 2017 (CN) .......................... 201710798308.9

(51) Int. Cl.
| | |
|---|---|
| A61K 47/54 | (2017.01) |
| A61K 9/19 | (2006.01) |
| A61K 31/337 | (2006.01) |
| A61K 47/26 | (2006.01) |
| A61K 47/40 | (2006.01) |

(52) U.S. Cl.
CPC .............. *A61K 47/542* (2017.08); *A61K 9/19* (2013.01); *A61K 31/337* (2013.01); *A61K 47/26* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 5,438,072 A | 8/1995 | Bobee et al. | |
| 5,698,582 A | 12/1997 | Bastart et al. | |
| 5,714,512 A | 2/1998 | Bastart et al. | |
| 9,085,605 B2 | 7/2015 | Liu et al. | |
| 2008/0262078 A1 | 10/2008 | Namdeo et al. | |
| 2009/0215882 A1 | 8/2009 | Bouzada et al. | |
| 2009/0215883 A1* | 8/2009 | Bouzada ................. | A61K 9/19 514/449 |
| 2010/0267817 A1 | 10/2010 | Jang et al. | |
| 2013/0046000 A1* | 2/2013 | Kitamoto ........... | A61K 31/4545 514/373 |
| 2013/0143826 A1 | 6/2013 | Liu et al. | |

FOREIGN PATENT DOCUMENTS

| | | |
|---|---|---|
| CN | 101002761 A | 7/2007 |
| CN | 101396354 A | 4/2009 |
| CN | 101868232 A | 10/2010 |
| CN | 102274190 A | 12/2011 |
| CN | 106589055 A | 4/2017 |
| EP | 0593601 A1 | 12/1997 |
| EP | 1982699 A1 | 10/2008 |
| JP | 2010536837 A | 12/2010 |

OTHER PUBLICATIONS

English machine translation for CN102274190 (online). Obtained from the internet: <https://patents.google.com/patent/CN102274190B/en?oq=cn+102274190>. (Year: 2011).*

(Continued)

*Primary Examiner* — Katherine Peebles
(74) *Attorney, Agent, or Firm* — Duane Morris LLP

(57) ABSTRACT

The present invention belongs to the field of pharmaceutical manufacturing technology. The present invention provides a pharmaceutical composition of a conjugate and a preparation method thereof. The pharmaceutical composition is preferably administered by injection. The docetaxel conjugate has a structural formula as shown in the following formula: (I).

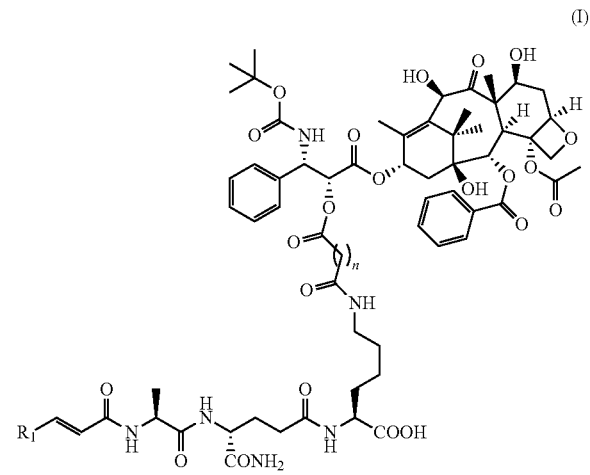

13 Claims, 3 Drawing Sheets

(56) References Cited

OTHER PUBLICATIONS

English machine translation for CN106589055 (online). Obtained from the internet: <https://patents.google.com/patent/CN106589055A/en?oq=cn+106589055> (Year: 2017).*

Jiansu CN 101396354 English Machine Translation [online]. Google Patents. Apr. 1, 2009 [Retrieved on Jan. 6, 2022]. Retrieved from the internet: <https://patents.google.com/patent/CN101396354B/en?oq=CN+101396354+>. (Year: 2009).*

Teagarden et al. European Journal of Pharmaceutical Sciences, vol. 15, pp. 115-133. (Year: 2002).*

Human Translation of Tsinghua CN 106589055; publication date: Apr. 26, 2017; provided to the USPTO by Schreiber Translations, Inc. Jan. 2022. (Year: 2022).*

Amide entry in New World Encyclopedia [online]. New World Encyclopedia, available online from at least 2016 [retrieved on Apr. 24, 2023]. Retrieved from the internet: <https://www.newworldencyclopedia.org/entry/Amide#:~:text=They%20are%20significantly%20less%20water,be%20H%2Dbond%20acceptors).> (Year: 2016).*

European Patent Office, Supplementary European Search Report issued in corresponding European Application No. 18853850.8, dated Mar. 24, 2021.

Chinese Patent Office, Office Action dated Sep. 28, 2021, for corresponding Chinese Patent Application No. 201880058024.9 (English translation provided).

Chinese Patent Office, Office Action dated Mar. 3, 2022, for corresponding Chinese Patent Application No. 201880058024.9 (English translation provided).

Japanese Patent Office, Search Report dated May 25, 2022, for corresponding Japanese Patent Application No. 2020-513869 (English translation provided).

Japanese Patent Office, Notice of Reasons for Rejection dated May 19, 2022, for corresponding Japanese Patent Application No. 2020-513869 (English translation provided).

Li et al., Chemical conjugation of muramyl dipeptide and paclitaxel to explore the combination of immunotherapy and chemotherapy for cancer, Glycoconj J (2008) 25:415-425.

* cited by examiner

PHARMACEUTICAL COMPOSITION OF DOCETAXEL CONJUGATE AND PREPARATION METHOD

PRIORITY CLAIM AND CROSS REFERENCES

The present application is a National Stage Application, filed under 35 U.S.C. 371, of International Patent Application No. PCT/CN2018/103887, filed on Sep. 4, 2018 and published as WO 2019/047812, which claims for the priority of Chinese Patent Application No. 201710798308.9, filed on Sep. 7, 2017, each of which is incorporated here by reference in entirety.

FIELD OF THE INVENTION

The present invention belongs to the field of pharmaceutical manufacturing technology, particular relates to a pharmaceutical composition of a docetaxel conjugate and a preparation method.

BACKGROUND OF THE INVENTION

Malignant tumor is a key threat to human health currently. Tumor metastasis is one of the essential features of malignant tumor and the most fundamental reason of treatment failure, and about 80% or more tumor patients in clinical die of metastasis of malignant tumor. Taxanes, including taxol and docetaxel, exhibit low oral bioavailability, mainly resulting from efflux mediated by the p-glycoprotein on the intestinal epithelial cells, liability to CYP450 mediated metabolism and low water-solubility. Because taxanes are still the first-line drugs in their therapeutic field, the various researches on taxanes are hot-spots for medicinal chemists. Since the idea of conjugation of natural anti-tumor drug molecules with immune stimulators was put forward, new progresses in searching anti-metastasis drug molecules by combining chemotherapy and immunotherapy have been achieved.

Pharmaceutical compositions may be prepared to various dosage forms for clinical use. Among them, new forms for parenteral administration include injections and powder injections. Surfactants are used to increase the solubility in commercially available taxane antitumor drugs. Among them, paclitaxel injections are mostly prepared by dissolving drug and polyoxyethylene castor oil in anhydrous ethanol solution. Before clinical use, they are dissolved and diluted with infusion. The ratio of polyoxyethylene castor oil to drug in the paclitaxel injections is about 88:1. The docetaxel injections are mostly prepared by dissolving docetaxel in Tween. In clinical use, they are dissolved with an ethanol-containing aqueous solution. The ratio of Tween to drug in the docetaxel injections is 27:1. Safety studies have shown that non-ionic surfactants have certain allergic and hemolytic properties when used by injection. Large quantities of surfactants can cause serious side effects, which limits the clinical use of these drugs. Due to the side effects of taxanes and non-ionic surfactants, patients need to be desensitized with corticosteroids and antihistamines before using paclitaxel and docetaxel injections. In addition, the presence of high-concentration surfactants in the infusion will have a dissolution effect on the plasticizer in plastic infusion bottles (especially PVC infusion bottles), causing the plasticizer to enter the infusion and increase the particles in the infusion. In addition, ethanol is added in the commercial docetaxel injections and paclitaxel injections to promote drug reconstitution, which will increase the toxicity of organic solvents after injection. For different specific drugs, ensuring storage stability is a basic guarantee for achieving clinical drug safety.

Docetaxel is a taxane drug with better effect in clinical application currently, which is a semi-synthetic antitumor drug developed by the French Rhone-Poulenc Rorer Co., Ltd. and first marketed in 1995. Because docetaxel is insoluble in water, the methods of adding surfactant and an organic solvent are adopted to improve the solubility of docetaxel.

Chinese patent applications 02147245.9, 93119653.1, and French patent application 9108527 described an injectable composition that was prepared by blending taxane compounds such as docetaxel, diluents such as ethanol, and surfactants, and removing the ethanol under vacuum, to obtain a stable drug-containing solution. The solution was diluted with water or an aqueous solution containing sorbitol, glucose, propylene glycol, sodium chloride, etc., and the mixed liquid was used as a drug solution for preparing a clinical infusion.

U.S. Pat. Nos. 5,698,582 and 5,714,512 disclosed a method for preparing docetaxel stock solution by dissolving docetaxel in anhydrous ethanol, adding Tween 80 and removing the ethanol by rotary evaporation under reduced pressure, to obtain the stable stock solution. When the stock solution was diluted with 5% glucose infusion to a concentration of 0.1, 0.3, and 0.5 mg/ml, the resulting diluents were also stable.

Chinese patent CN200610032942 disclosed that adding an antioxidant to the prescription can improve the stability of the preparation. Citric acid, polysorbate 80 and the prescribed amount of docetaxel were mixed in an appropriate amount of absolute ethanol and stirred until a clear and homogeneous solution was obtained. After evacuating the ethanol under reduced pressure, the residues were sub-packed to penicillin bottles. Stability retention test showed that the preparation had good stability and the validity period was extended to 1.5 years without deterioration. Chinese patent CN200710162304.8 provided a liquid composition, which was a surfactant solution in which a taxane compound is dissolved. The pH value of the solution was 5 or less, preferably 3-5. The liquid composition was particularly suitable for use as an injection preparation, and was stable during storage, and safer and more effective.

The taxane drugs and Tween 80 were mixed in all the above preparation methods. Since the drug exists in a dissolved state, the instability of the drug is increased. In addition, the large-amount used surfactant and the ethanol aqueous solution used in the drug-containing solution or reconstitution solvent thereof, reduce the clinical safety of the drug.

The solutions for stability and solubility in the prior art could not solve the corresponding problems for the polypeptide conjugated drugs of the present invention. It has been a difficult problem that the large amount of existing surfactants caused safety issues.

The technical problem to be solved by the present invention is to provide a taxane drug composition with higher stability, improve the stability of the drug, reduce the use of surfactants and organic solvents, and significantly improve the safety.

SUMMARY OF THE INVENTION

The technical problem to be solved by the present invention is to provide a taxane drug composition with higher stability, improve the stability of the drug, reduce the use of surfactants and organic solvents, and significantly improve the safety.

In the present invention, the docetaxel conjugate (polypeptide derivative) and a surfactant-containing reconstitution solvent are separately prepared. The lyophilized powder injection of the docetaxel conjugate exists in a solid form, rather than a solution containing surfactant, and thus the stability of the drug is significantly improved. Since docetaxel conjugate is stable under weakly acidic conditions but has poor solubility, whereas it is easily degraded under neutral or weakly alkaline conditions but has high solubility, the present invention takes the stability and solubility of the drug into account at the same time. The buffer solution is added to the lyophilized powder injection to adjust the pH value to be weakly acidic (3.0-7.0, particularly preferably 4.5-5.5), so as to improve the stability of the drug. Meanwhile, an aqueous solution containing a small amount of a surfactant is used as a reconstitution solvent. The reconstitution solvent is added to the lyophilized powder injection before clinical use, and the drug can be quickly reconstituted. The reconstituted solution is further diluted with a 5% glucose infusion, 0.9% sodium chloride infusion or sodium lactate Ringer's infusion to the concentration used clinically before the infusion was performed.

In the present invention, no organic solvent is added, and only ≤5 times drug amount of the surfactant is added to solubilize the drug, compared with 27 times drug weight of Tween 80 added in the marketed docetaxel injection and 88 times the drug weight of polyoxyethylene castor oil added in the marketed paclitaxel injection, while ethanol is added in both of commercial docetaxel and paclitaxel injection to solubilize. The amount of surfactant used in the present study is much lower, which greatly improves the safety in clinical administration.

The docetaxel conjugate is obtained by linking docetaxel with a preferred potent immunopotentiator, muramyl dipeptide, to achieve dual-function of anti-tumor and anti-tumor metastasis by combining chemotherapy and immunotherapy. It has stronger antitumor activity than docetaxel.

The docetaxel conjugate may play an anti-tumor role by interfering with the mitosis of the cells and the microtubule network necessary for cell function during division. Due to its molecular structure, the derivative has both the properties of taxane compounds and certain characteristics of small molecule immune enhancers, and is almost insoluble in water.

Specifically, the molecular formula of the docetaxel conjugate is as follows:

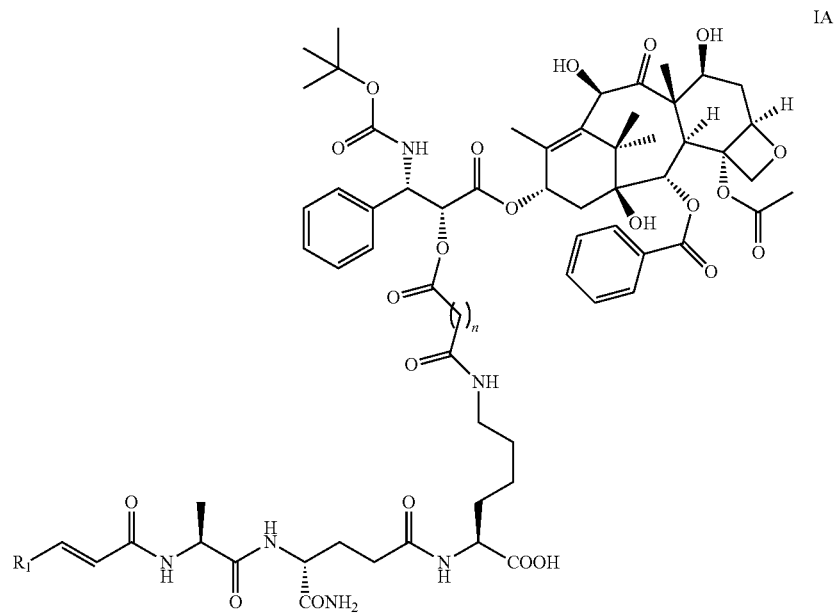

IA

Wherein, $R_1$ is selected from phenyl or one or more halogen-substituted phenyl, halogen is selected from fluorine, chlorine, bromine, or iodine, n is a natural number of 2 to 5, and is selected from 2, 3, 4, or 5.

The docetaxel conjugate is selected from the group consisting of:
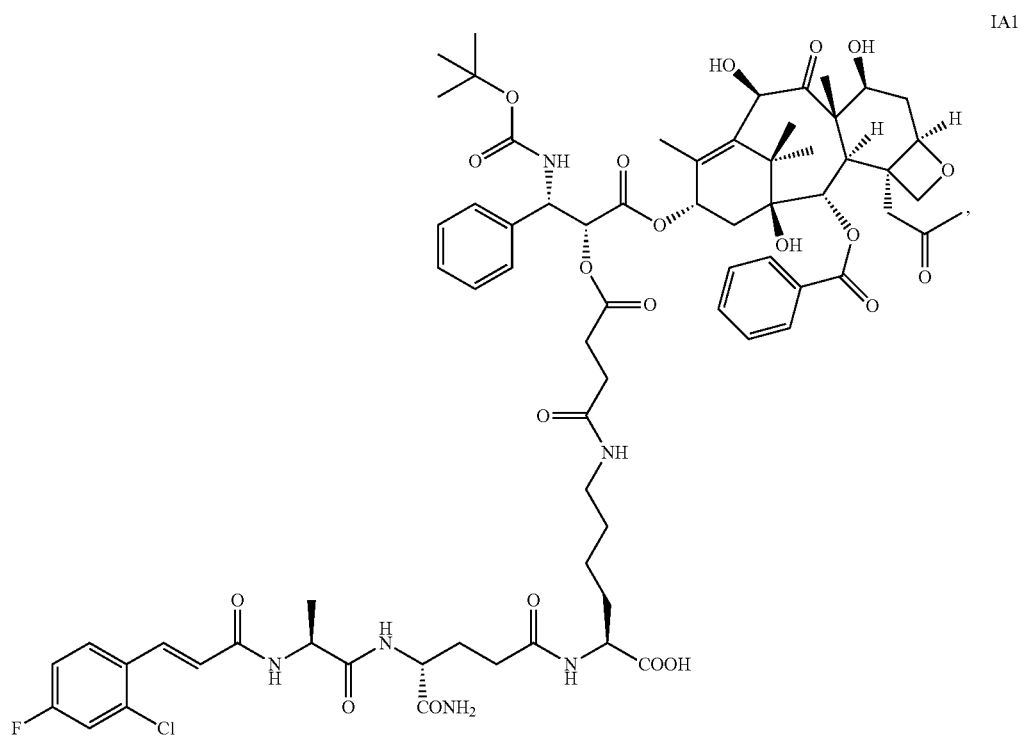
IA1
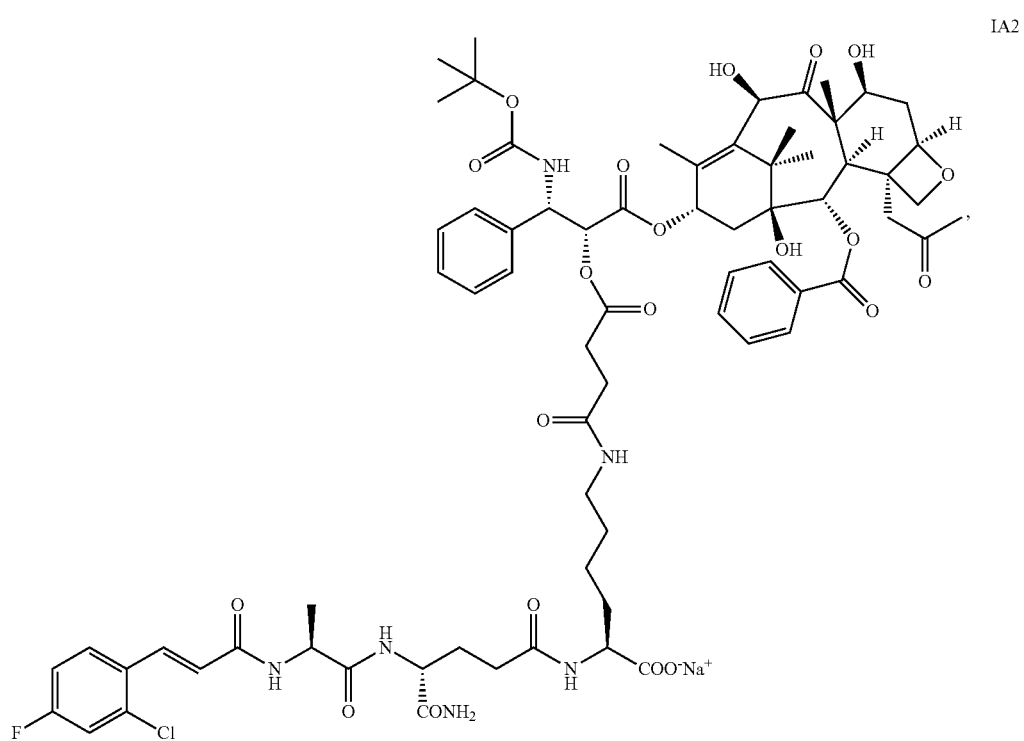
IA2

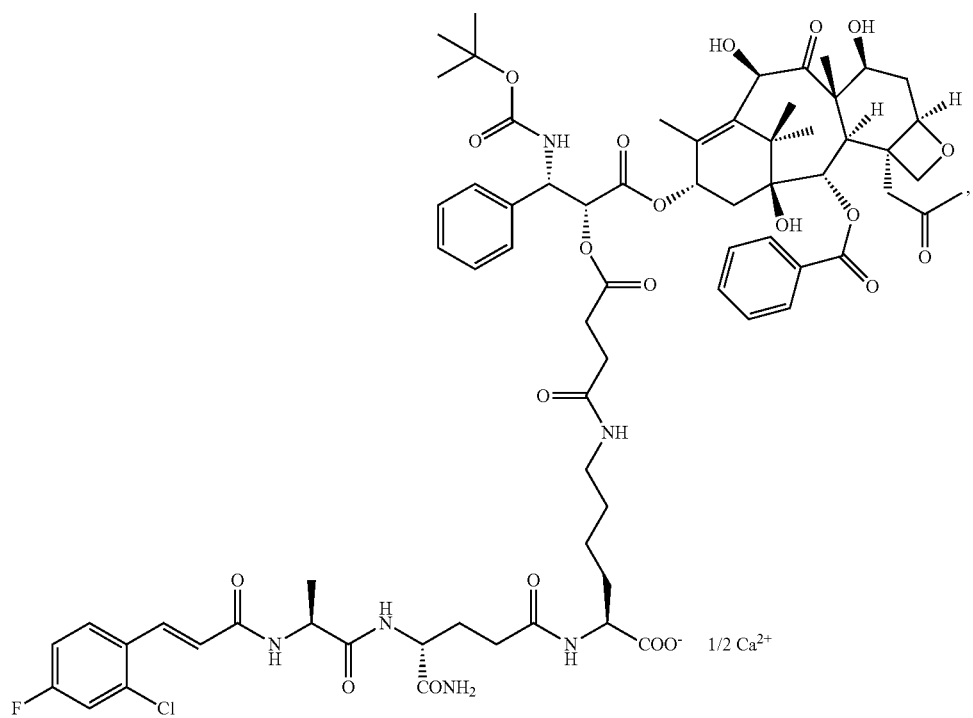
IA3
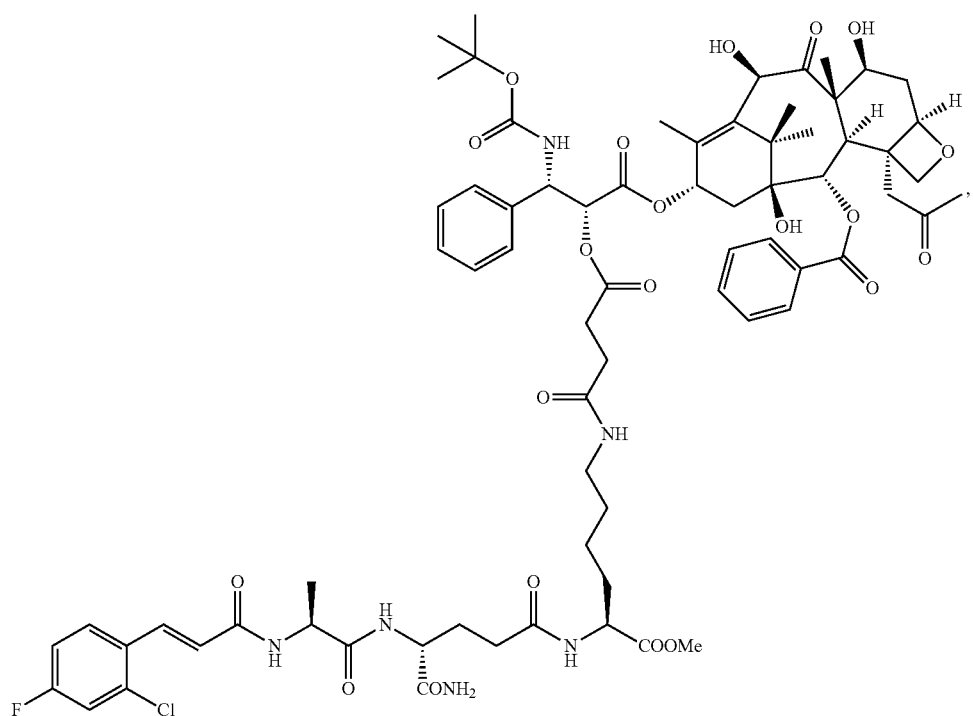
IA4

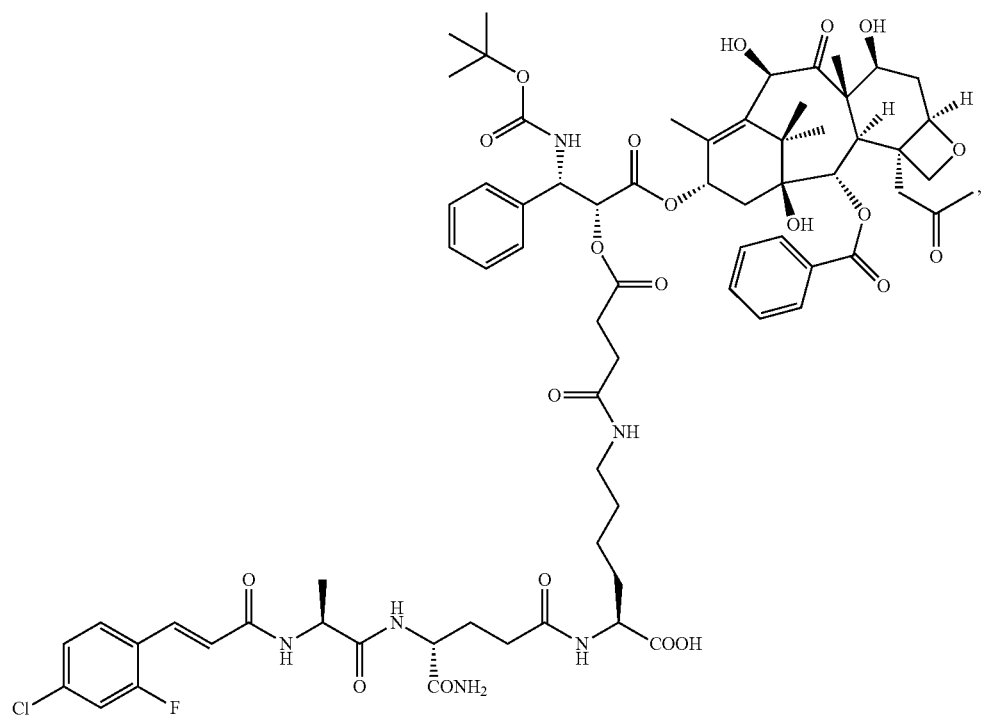
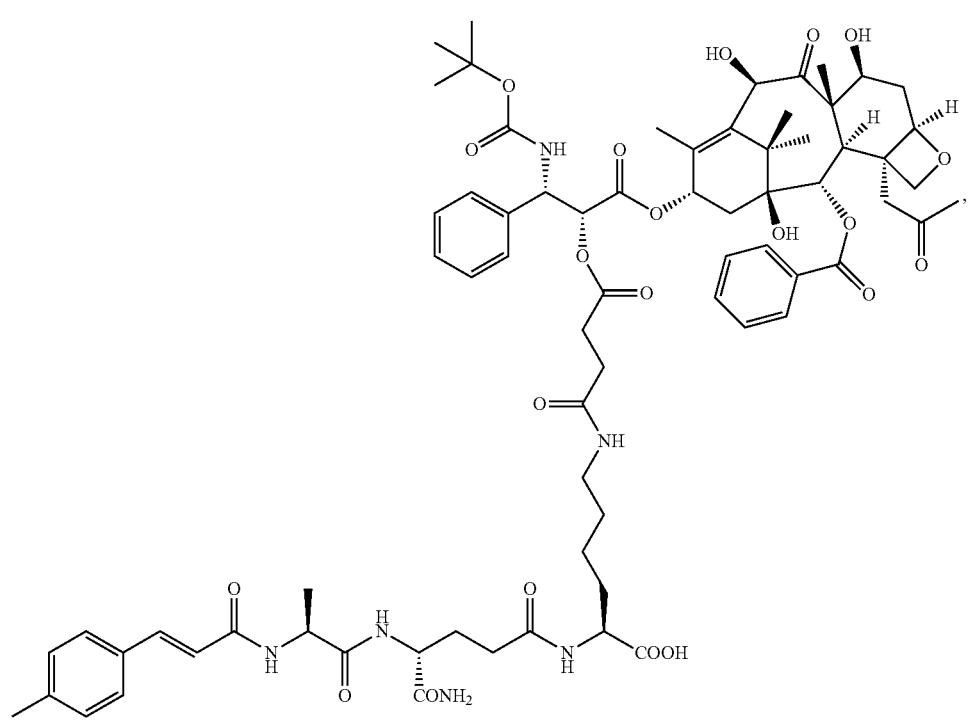

-continued
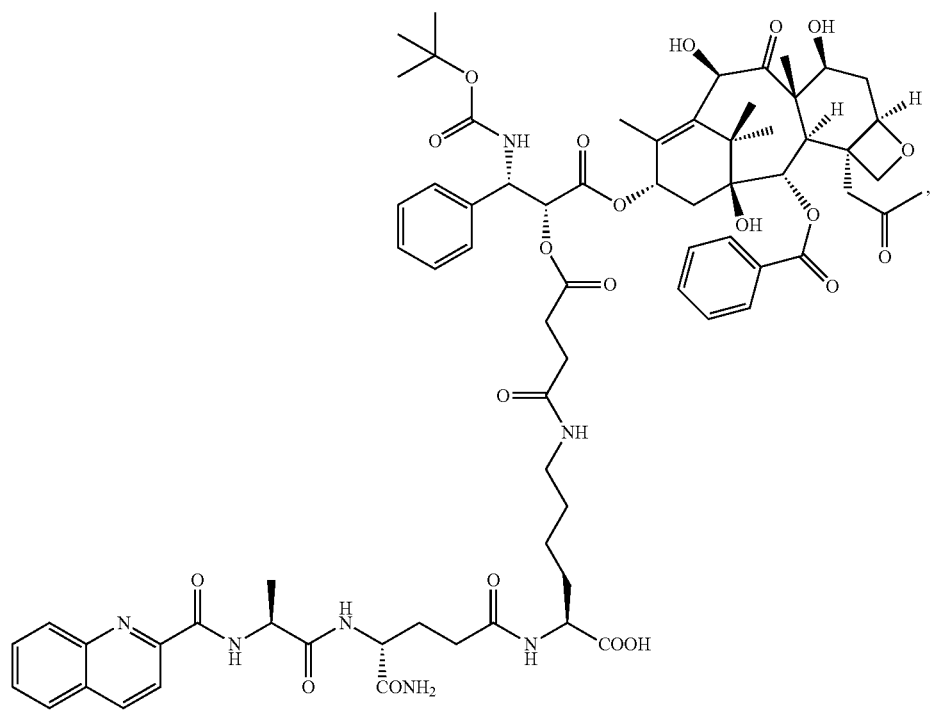
IA7
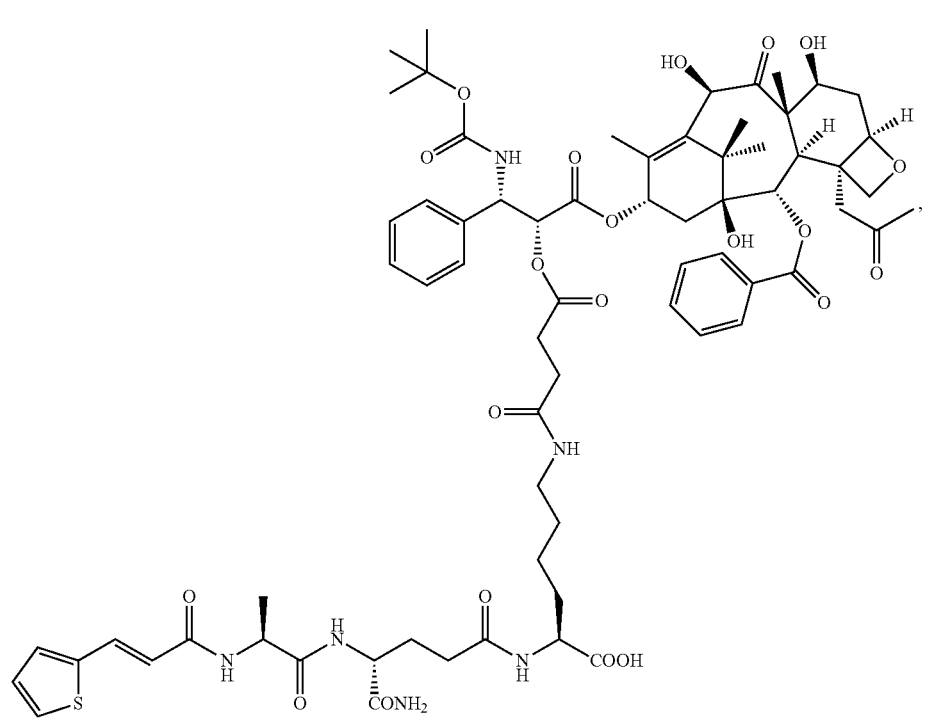
IA8

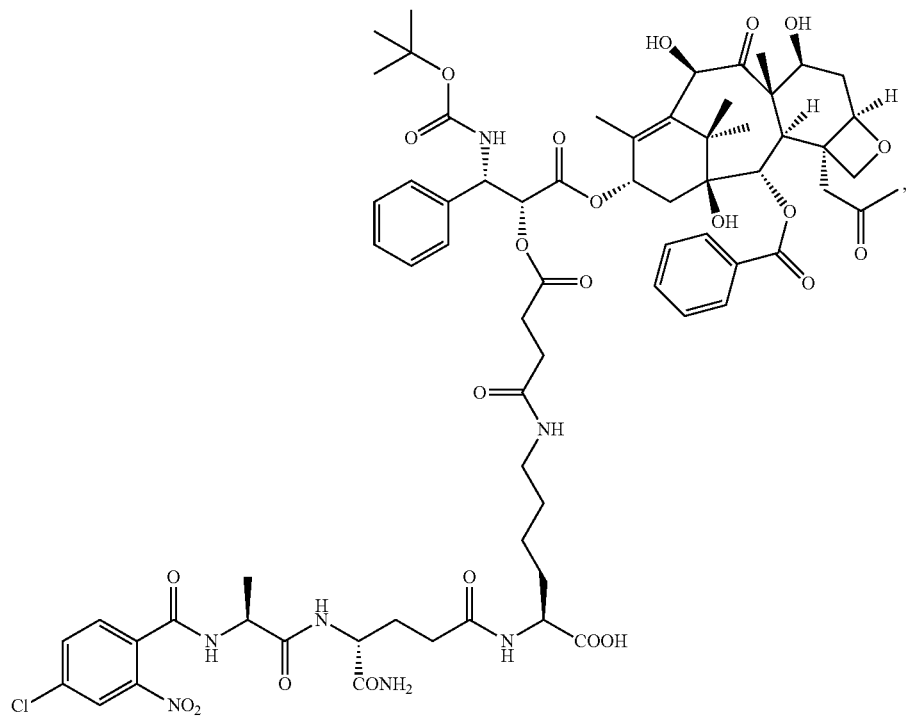
IA9
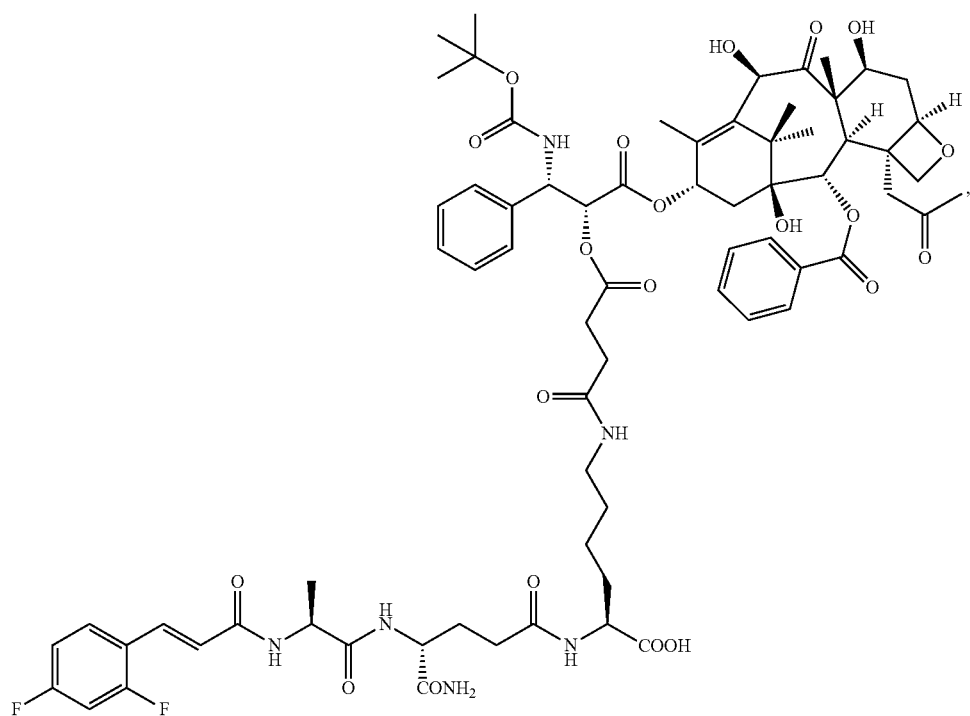
IA10

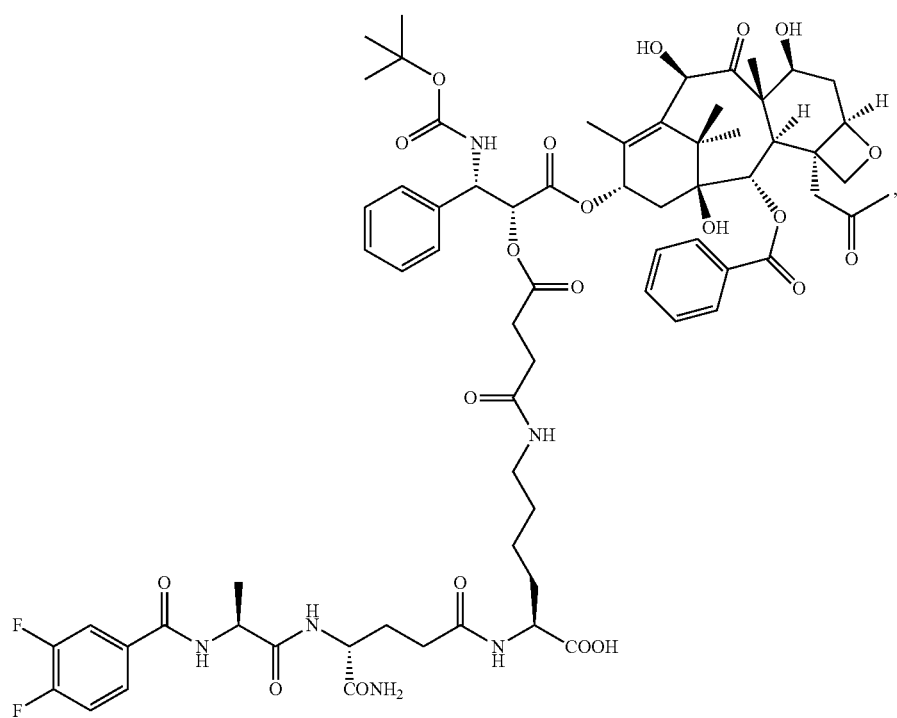
IA11
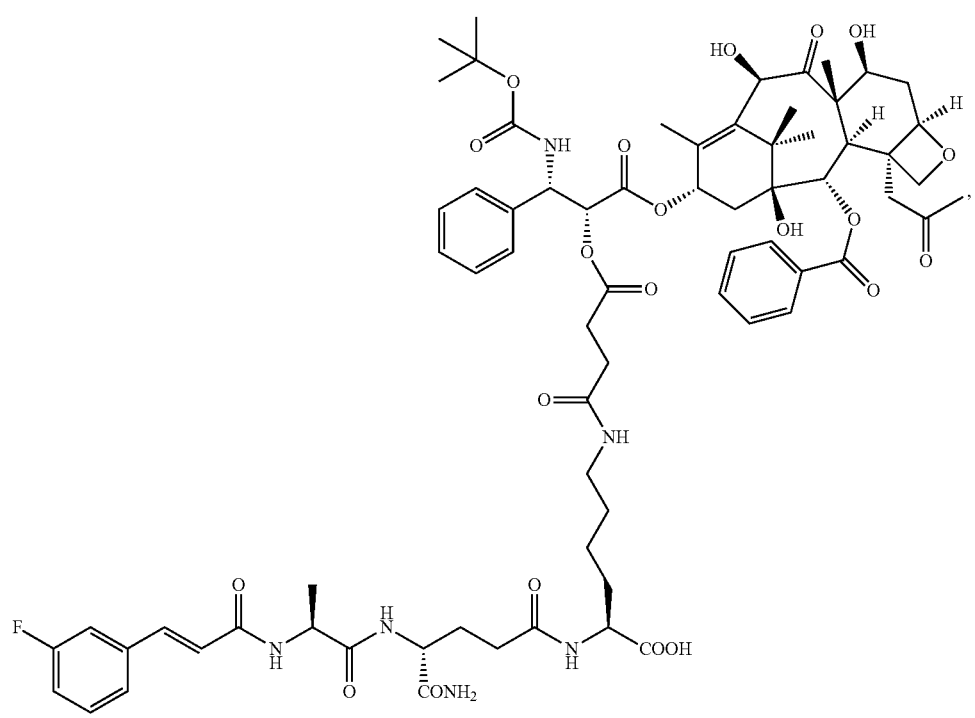
IA12

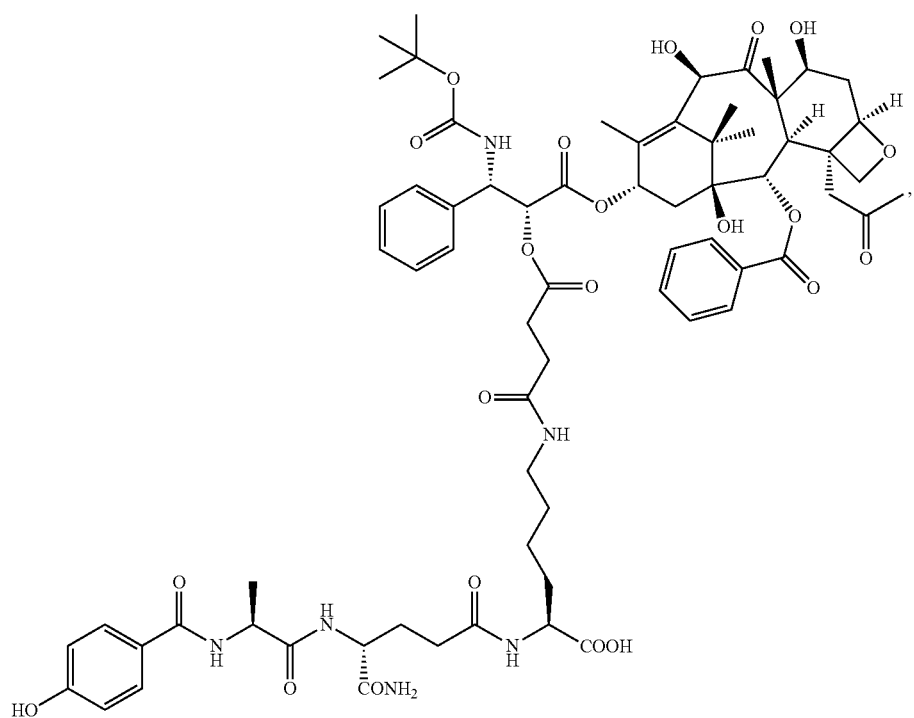
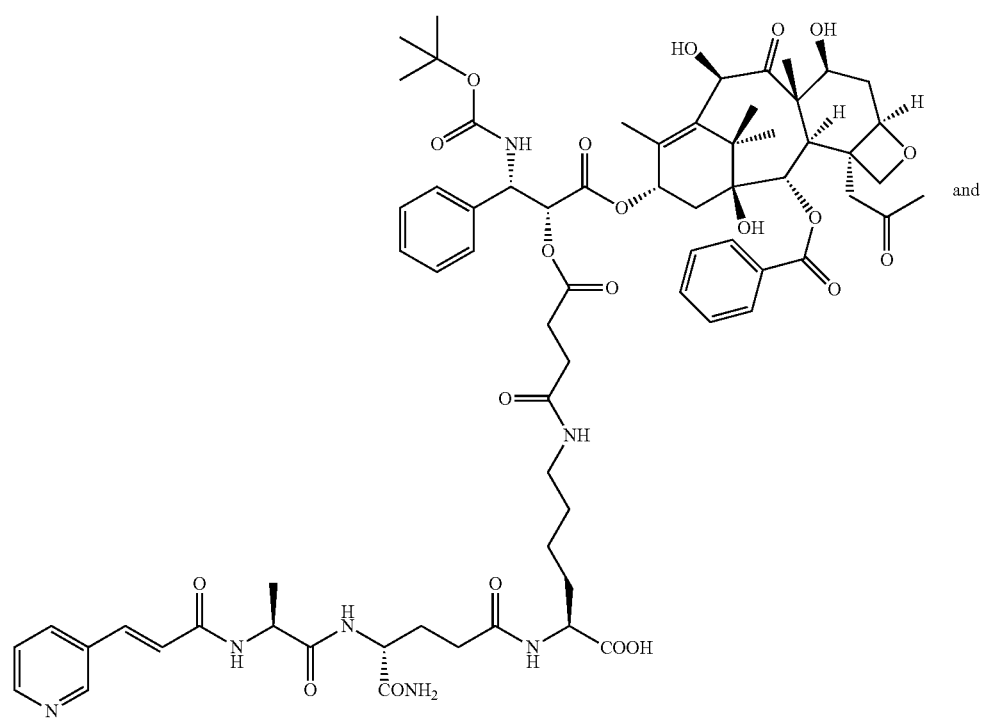

-continued

IA15

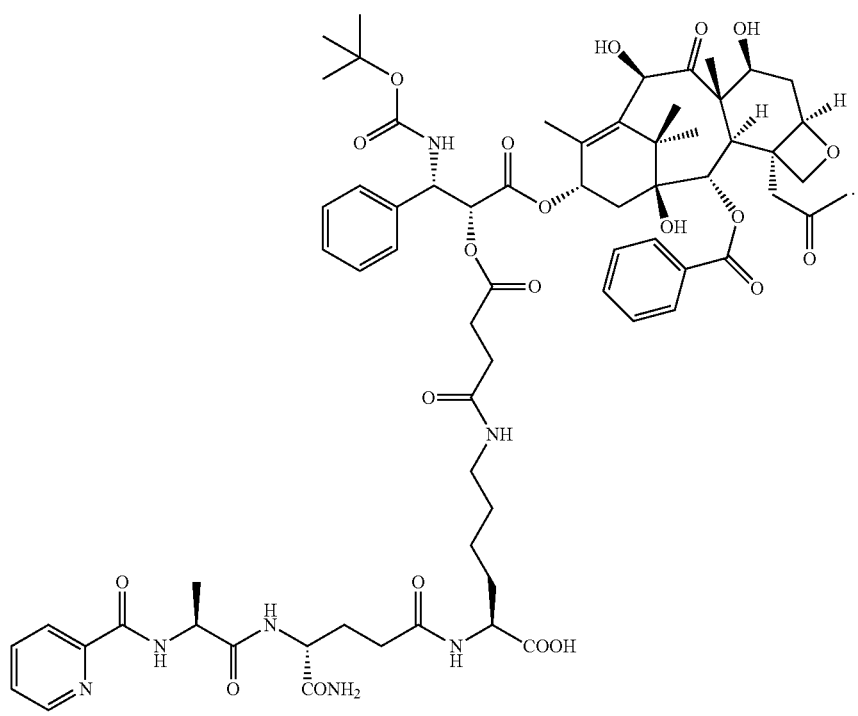

Specifically, the docetaxel conjugate composition described in the present invention includes: (1) a docetaxel conjugate composition and one or more pharmaceutically acceptable carriers, which have no surfactant, and the pH value of the composition ranges from 3.0 to 7.0; and (2) another reconstitution solvent separated into different chambers, which contains one or more surfactants at 0.1 to 15 parts by weight, based on 1 part by weight of the docetaxel conjugate. The different chambers may be two separated portions of the same container, or may be separated portions of two different containers and the like.

The pharmaceutically acceptable carrier is one or more selected from the group consisting of fillers and pH adjusting agents.

One of the preferred embodiments is that the pharmaceutically acceptable carrier is selected from one or more fillers, the weight of the filler is 1 to 100 parts by weight, preferably 3 to 20 parts by weight, based on 1 part by weight of the docetaxel conjugate.

The filler is one or more selected from the group consisting of mannitol, sucrose, glucose, trehalose, dextrose, lactose, hydroxyethyl starch, sulfobutyl-O-cyclodextrin, O-cyclodextrin, polyvinylpyrrolidone, histidine, valine, threonine, glycine, arginine, xylitol, sorbitol, fructose, poloxamer, gelatin, chitosan, sodium chloride and albumin; preferably mannitol.

Another one of the preferred embodiments is that the pharmaceutically acceptable carrier is selected from one or more kinds of pH adjusting agents, and the pH adjusting agent is one or more selected from the group consisting of sodium hydroxide, potassium hydroxide, sodium dihydrogen phosphate, disodium hydrogen phosphate, potassium dihydrogen phosphate, dipotassium hydrogen phosphate, hydrochloric acid, citric acid, tartaric acid, acetic acid, malic acid, phosphoric acid, nitric acid, and sulfuric acid. In a preferred embodiment, the buffer composition composed of the aforementioned alkaline pH adjusting agent and acidic pH adjusting agent, for example, the acid-base adjusting agents are sodium dihydrogen phosphate and sodium hydroxide. The pH value of the composition preferably ranges from 4.5-5.5.

Through the selection of the raw and auxiliary materials mentioned above, the solubility and stability of the pharmaceutical composition are ensured as much as possible in the absence of a surfactant. Among them, when the pH of the composition is greater than 7.0, its stability is significantly deteriorated, which makes it difficult to meet the requirements for long-term storage of drugs; and when the pH of the composition is less than 3.0, the ratio of the solubility of the pharmaceutical composition relative to that of the pharmaceutical composition at pH 5.0 is reduced to less than 1/20. The reduced solubility greatly increases the time required for reconstitution, and the reconstitution effect is poor. Preferably, the pH value of the pharmaceutical composition is 4.5-5.5, which has more excellent effects on reconstitution and storage stability.

In the present invention, it has been found in a large number of experimental studies that if a drug is prepared by mixing it with a solubilizing agent such as a surfactant, the solubilizing agent will make the docetaxel conjugate in a liquid or semi-liquid state in the preparation, from which the water is difficult to be removed. During the storage, the drug is prone to degradation reactions such as hydrolysis, and the stability is significantly deteriorated.

For clinical needs, the reconstitution solvent and the docetaxel conjugate composition with a surfactant-free carrier are mixed before injection to make the composition have a more suitable dissolving effect, avoiding the influence of the reconstitution solvent on the storage of the pharmaceutical composition. The reconstitution solvent contains one or more less amount of surfactants and water for injection, wherein the amount of the surfactant used is very small.

The above-mentioned reconstitution solvent contains one or more surfactants at preferably 3-10 parts by weight, based on 1 part by weight of the docetaxel conjugate, which can reduce the adverse reactions such as allergy and hemolysis caused by the use of the surfactant as much as possible, improve the patient's tolerance to the drug and increase the clinical administration dose. It can also reduce the pretreatment before drug administration for preventing the toxic and side effects of the drug. Due to the composition of the raw and auxiliary materials of the above-mentioned composition and the selection of the reconstitution solvent, the use of organic solvents such as ethanol is avoided, and the toxic and side reactions caused by ethanol are minimized.

The surfactant in the reconstitution solvent is one or more selected from the group consisting of amphoteric surfactants and non-ionic surfactants. The amphoteric surfactant is one or more selected from the group consisting of soya phospholipid, egg yolk phospholipid, phosphatidylcholine, phosphatidylethanolamine, serine phospholipid, inositol phospholipid, phosphatidic acid, cerebrolipid and hydrogenated phospholipid; non-ionic surfactant is one or more selected from the group consisting of Tween, Span, sucrose fatty acid esters (such as sucrose esters), polyoxyethylene fatty acid esters (such as Myrij), polyoxyethylene fatty alcohol ethers (such as Brij), and poloxamers.

Based on a large number of experiments, Tween (Polysorbate-80), polyoxyethylene castor oil EL35, polyethylene glycol stearate 15, and poloxamer 188 are preferred. The composition is reconstituted by using the above reconstitution solvent to obtain a reconstituted solution to improve the solubility of the drug in the injection solvent. The reconstituted solution can be dissolved in a conventional infusion medium, such as a 5% glucose aqueous solution, 0.9% sodium chloride infusion or sodium lactate Ringer for intravenous infusion.

The object of the present invention is also to provide an industrially implementable method for the preparation of a docetaxel conjugate composition with low toxicity, good water solubility, and improved stability. The composition is preferably a lyophilized powder preparation or injection liquid.

Specifically, the preparation method includes the steps of: dissolving the raw and auxiliary materials of the above-mentioned composition (1) by using a solvent, adjusting the pH value to the desired range, and preparing by lyophilization.

A preferred method for preparing the reconstitution solvent (2) includes the steps of: weighing the prescribed amount of surfactant, adding the prescribed amount of water, stirring until dissolved, filling with nitrogen to make the oxygen content in the headspace ≤7%, corking, capping and sterilizing.

The reconstitution solvent in the composition is prepared separately, which not only minimizes the amount of surfactant used in the composition, but also improves the stability of the drug. In addition, in order to accelerate the dissolution of the raw and auxiliary materials, and ensure the lyophilized state of the composition, such as color and appearance, the influence of moisture residue on the stability of the composition is reduced as much as possible.

The present invention further provides a method for preparing the foregoing composition. The method for preparing the composition (1) includes the steps of: adding the filler to a certain amount of a solvent, stirring to dissolve, adding docetaxel conjugate and stirring, and after the docetaxel conjugate is uniformly dispersed, further adding or not adding a suitable solvent that is the same as or different from the aforementioned solvent to completely dissolve the drug, and freeze drying to remove the solvent.

The solvent is one or more selected from the group consisting of water, tert-butanol, ethanol, propylene glycol, polyethylene glycol, and cyclohexane, preferably tert-butanol.

The solvent is further preferably a combination of water and one or more of tert-butanol, ethanol, propylene glycol, and polyethylene glycol in a certain ratio. The amount of the solvent can be appropriately adjusted according to the lyophilization process. In the aqueous solvent, the weight of one or more of tert-butanol, ethanol, propylene glycol, and polyethylene glycol is preferably 0.1 to 98 parts by weight, based on 1 part by weight of water; a mixed solvent of water and tert-butanol is preferred, with a weight ratio of 1:0.1 to 1:5, particularly preferably 1:0.5. The suitable solvent has substantially no residue after lyophilization, which reduces as much as possible its impact on the safety of clinical use.

A large number of experimental studies have found that the drug is dissolved by mixing the lyophilized powder composition made of docetaxel conjugate and the filler as well as the separately prepared reconstitution solvent before clinical use. Lyophilized powder composition is an effective method for preserving drugs. In the freeze-drying process, the product to be dried is frozen at a low temperature, and then dried in a vacuum environment, so that the organic solvent and/or moisture is directly lifted from the solid state into steam and removed from the product to make the product dry. This method effectively prevents the changes in the physicochemical and biological properties of the product, and effectively protects the stability of the heat-sensitive drug. The product has a loose shape and almost no change in color after drying, and can quickly dissolve and restore the physicochemical properties and biological activity of the original aqueous solution after adding the solvent. The freeze-drying process can control the solvent residue in the lyophilized powder to a very low level, which can improve the stability for readily hydrolyzable drugs and reduce the possibility of microbial pollution. Drying is performed under vacuum conditions. After the freeze-drying process, it can be filled with an inert gas, which protects the readily oxidizable drugs. The preparation of the drug into a lyophilized powder injection can extend the shelf life of the product or relax the storage conditions, making it easier to transport.

In the preferred embodiment of the present invention, suitable solvents such as water and tert-butanol are used to form an aqueous solvent for the preparation of the solution before lyophilization, improving the solubility of the drug. The selected suitable solvent is a good lyophilized solvent with the characteristics of miscibility with water and low toxicity.

The beneficial effects of the present invention are mainly reflected in:
  (1) In the composition of the present invention, adverse reactions caused by administration are reduced by decreasing the use of surfactants as much as possible and decreasing the use of organic solvents.
  (2) The lyophilized powder composition of docetaxel conjugate and the reconstitution solvent are prepared separately. Drug is dissolved by mixing both of them before clinical use. Because the drug and the reconstitution solvent containing solubilizer are separately prepared and stored, the stability of the drug is improved and the clinical use is safer.
  (3) In the preparation of the lyophilized powder composition of the present invention, a mixed solvent of water and organic solvents such as tert-butanol is used to solubilize the drug before freeze drying. The use of the mixed solvent can solve the problem of dissolution of poorly soluble drugs during lyophilization. Solvents such as tert-butanol have good freeze-drying properties and low toxicity.

DETAILED DESCRIPTION OF THE INVENTION

Figure 1:
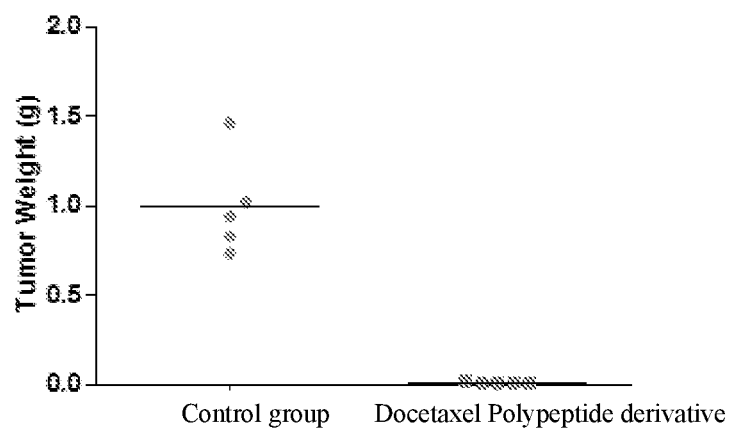
FIG. 1 is a graph showing the antitumor effect of docetaxel conjugate IA1 on MDA-MB-231 human breast cancer in mice.
Figure 2:
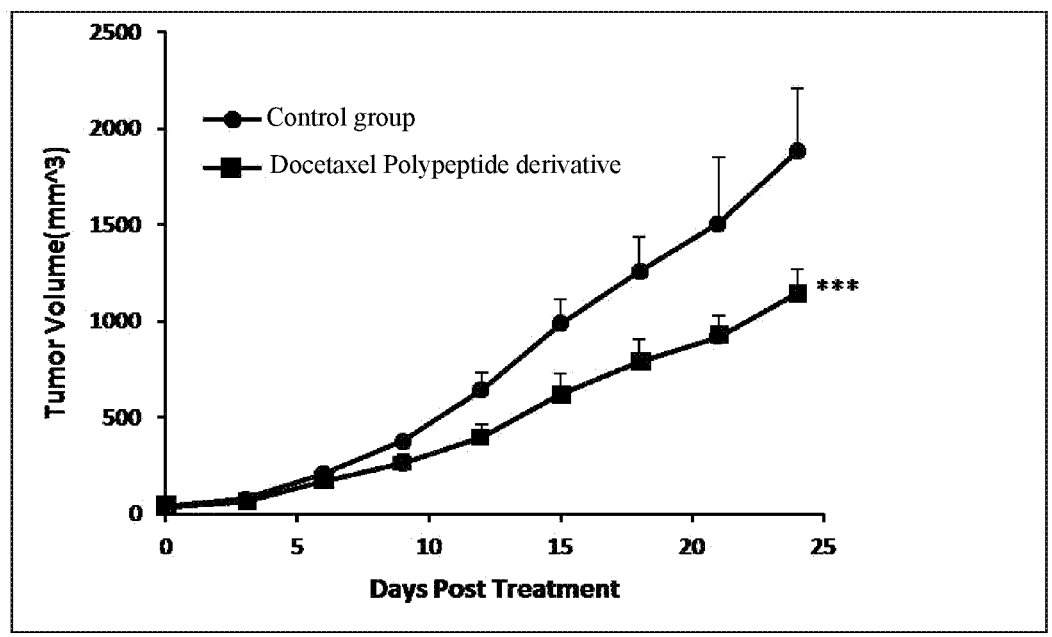
FIG. 2 is a graph showing the inhibitory effect of lyophilized powder injection of docetaxel conjugate IA1 on lung metastasis of 4T1 breast cancer in BALB/c mice.

In the following part, the present invention will be further explained through preferred embodiments and drawings, but the present invention is not limited to the following protection scope. In the following examples, unless otherwise stated, the docetaxel conjugate is selected from the aforementioned compound IA1 as representative.

The method for measuring the impurity content in the following examples is as follows, with reference to 0512 liquid chromatography method in the "Chinese Pharmacopoeia" 2015 Edition Volume IV. 20 μl of the system suitability solution, the reference solution, and the test solution are injected into the liquid chromatograph respectively, and the chromatograms are recorded. Calculation formula: each $$\text{each impurity content} = \frac{A_T \times C_S}{A_S \times C_T} \times F \times 100\%.$$

$A_T$ is the peak area of each impurity in the test solution; $A_S$ is the average peak area of the main peak in the reference solution; $C_T$ is the concentration (mg/ml) of the test solution; Cs is docetaxel conjugate concentration (mg/ml) in the reference solution; F is the correction factor for each impurity.

HPLC conditions: An octadecyl bonded silica gel column (C18, 4.6×150 mm, 3.5 μm); gradient elution, phase A: acetonitrile: 0.1% phosphoric acid=45:55, phase B: acetonitrile; detection wavelength: 225 nm; flow rate: 1.0 ml/min; column temperature: 40° C.

Example 1

The stability of IA1 in different pH environments and its solubility in different pH solvents are shown in Tables 1 and 2.

TABLE 1

The stability of IA1 in different pH environments

| Solvents | Time (h) | Decrease in purity of main peak within 14 h (%) |
|---|---|---|
| / | 0 h | — |
| Acetonitrile/pH 3.0 buffer | | 0.11 |
| Acetonitrile/pH 4.0 buffer | | 0.19 |
| Acetonitrile/pH 5.0 buffer | 14 h | 0.19 |
| Acetonitrile/pH 6.0 buffer | | 0.51 |
| Acetonitrile/pH 7.0 buffer | | 7.38 |
| Acetonitrile/pH 8.0 buffer | | 22.55 |

It can be seen from the above results that when the pH value is greater than 7.0, the impurity of the drug is extremely increased, which could not meet the demand for the medicinal content of active ingredients. When the pH is below 6.0, the impurity of the drug is significantly decreased.

TABLE 2

The solubility of IA1 in water, phosphate buffers with different pH values.

| Phosphate buffer | Solubility (mg/ml) |
|---|---|
| pH 5.5 | 0.223 |
| pH 4.5 | 0.037 |
| pH 3.5 | 0.008 |
| pH 3.0 | — |

However, when the pH of the composition is below 3.0, the solubility becomes significantly lower, which is almost the same as the solubility of the substance itself. It can be seen from the foregoing results that it has excellent solubility and stability at pH 4.5-5.5.

Example 2

Referring to the experimental results of Example 1, polysorbate 80, mannitol, glucose, lactose, sucrose, and sulfobutyl-β-cyclodextrin were selected as lyophilized fillers, as shown in Table 3 below.

Screening prescription of the kinds of filler of the prepared docetaxel conjugate IA1 (25 mg specification) (unit: mg/branch)

TABLE 3

| Composition (unit: mg) | Prescription 1 | Prescription 2 | Prescription 3 | Prescription 4 | Prescription 5 | Prescription 6 | Prescription 7 |
|---|---|---|---|---|---|---|---|
| IA1 | 25 | 25 | 25 | 25 | 25 | 25 | 25 |
| Polysorbate 80 (mg) | / | 125 | / | / | / | / | / |
| Mannitol (mg) | / | / | 150 | / | / | / | / |
| Sulfobutyl-β-cyclodextrin (mg) | / | / | / | 150 | / | / | / |
| Lactose (mg) | / | / | / | / | 150 | / | / |
| Sucrose (mg) | / | / | / | / | / | 150 | / |
| Glucose (mg) | / | / | / | / | / | / | 150 |
| Water for Injection (mg) | 2000 | 3000 | 2000 | 2000 | 2000 | 2000 | 2000 |
| Tert-butanol (mg) | 780 | 780 | 780 | 780 | 780 | 780 | 780 |
| Total impurity change % | 0.03 | 1.48 | 0.04 | 0.04 | 0.08 | 0.05 | 0.06 |

The corresponding filler was added to the above amount of water for injection and stirred to dissolve. Docetaxel conjugate IA1 was added and stirred to uniformly disperse. Then tert-butanol was added to enable IA1 to be dissolved. After filtration through a 0.22 μm filter membrane, the filtrate was divided into 15 ml vials, lyophilized and capped.

The total impurity change % refers to the amount of total impurity change relative to the drug substance after freeze-drying of the prescription composition. It can be seen that the total impurity increases significantly in the prescription using surfactant polysorbate 80 as a filler, which significantly affects the subsequent stability. In the case of no filler added in prescription 1, the reconstitution rate is very slow, and it cannot meet the expected ideal clinical requirements.

Example 3

On the basis of prescription 3 in Example 2, ethanol, propylene glycol, and polyethylene glycol were selected as the dissolving solvent in place of tert-butanol.

TABLE 4

| Prescription composition (unit: mg) | Prescription 3 |
|---|---|
| IA1 (mg) | 25 |
| Mannitol (mg) | 150 |
| Prepared dissolving solvents (mg) | 2780 |
| Reconstitution time | 5 min-10 min |
| Total impurity in 10 days at 40° C. | <1.5% |

Preparation method was the same as in Example 2. It was found that the reconstitution and stability using tert-butanol as a single solvent were better than other dissolving solvents. Some of the solvents resulted in unevenness or were difficult to be completely removed after lyophilization.

Note: The dissolving solvent is basically evaporated after lyophilization, which does not affect the safety of subsequent use of the drug.

Example 4

According to the result of Example 3 and the cost of the solvent, effects on the preparation with different proportions of water and tert-butanol were examined.

The ratio of tert-butanol to water in the intermediate solution of docetaxel conjugate IA1 for injection (25 mg specification).

TABLE 5

| | Prescription composition | | | | |
|---|---|---|---|---|---|
| | Prescription 9 | Prescription 10 | Prescription 11 | Prescription 12 | Prescription 13 |
| Docetaxel conjugate IA1 (mg) | 25 | 25 | 25 | 25 | 25 |
| Mannitol (mg) | 200 | 200 | 200 | 200 | 200 |
| pH value | 5.0 | 5.0 | 5.0 | 5.0 | 5.0 |
| tert-butanol (mg) | 1170 | 523 | 780 | 1037 | 585 |
| Water for injection (mg) | 1500 | 1330 | 2000 | 2670 | 2250 |
| tert-butanol/water for injection (v/v) | 1:1 | 1:2 | 1:2 | 1:2 | 1:3 |
| Total volume of tert-butanol and water for injection (ml) | 3 | 2 | 3 | 4 | 3 |

Note:
The density of tert-butanol was 0.78 g/cm$^3$.

According to the above prescription, considering the shape, reconstitution, moisture, solvent residues, and stability, 1:2 is the preferred volume ratio of tert-butanol to water as described in prescription 11. After comprehensive consideration, prescription 11 was selected, that is, the total volume of the 25 mg specification intermediate solution was 3 ml.

Example 5

Through the foregoing experiments, the buffer substances for adjusting the pH were selected. The effects of buffer pairs such as sodium dihydrogen phosphate/sodium hydroxide, acetic acid/sodium hydroxide on reconstitution were investigated. The properties of composition solution at pH 4.0, 4.5, 5.0 and 5.5 were further examined, as shown in below Table 6.

TABLE 6

Screening prescriptions of docetaxel conjugate IA1 for injection (25 mg specification) at different pH values (unit: mg/branch)

| Prescription composition | Prescription14 | Prescription15 | Prescription16 | Prescription 17 | Prescription 18 | Prescription 19 | Prescription 20 |
|---|---|---|---|---|---|---|---|
| IA1 (g) | 25 | 25 | 25 | 25 | 25 | 25 | 25 |
| Mannitol (g) | 200 | 200 | 200 | 200 | 200 | 200 | 200 |
| NaH$_2$PO$_4$/NaOH adjusted pH | / | 4.0 | 4.5 | 5.0 | 5.5 | / | / |
| AcOH/NaOH adjusted pH | / | / | / | / | / | / | 5.0 |
| tert-Butanol (mg) | 780 | 780 | 780 | 780 | 780 | 780 | 780 |
| Water for injection (mg) | 2000 | 2000 | 2000 | 2000 | 2000 | 2000 | 2000 |
| Reconstitution time | >5 min | 4 min | 2 min | 2 min | 2 min | >5 min | 2 min |
| Total impurity in 10 days at 40° C. | 1.40 | 1.12 | 1.34 | 1.33 | 1.38 | 1.45 | 2.33 |

Preparation method for prescription 14-20: Mannitol was dissolved in the above amount of water for injection under stirring. Docetaxel conjugate was added to the above solution and stirred to uniformly disperse. Then tert-butanol was added to completely dissolve the drug. The pH value was measured with or without addition of a certain amount of buffer substance, which should be consistent with the desired pH value. After filtration and sterilization through a 0.22 μm filter membrane, the filtrate was divided into 15 ml vials, freeze-dried, and capped.

It can be seen from the above results that the addition of fillers and suitable acid-base regulators can significantly shorten the reconstitution time. The use of sodium dihydrogen phosphate and sodium hydroxide as acid-base regulators has significantly better effects on stability and reconstitution at 4.5-5.5. Therefore, considering the stability and solubility, the pH adjusting agent of the pharmaceutical composition is preferably sodium dihydrogen phosphate and sodium hydroxide, and the pH is in the range of 4.5-5.5.

Example 6

In order to make the foregoing prescription more convenient in specific clinical use, the composition of the foregoing example further includes a reconstitution solvent that can achieve rapid reconstitution and excellent dissolution effect. It was found that preferably, polysorbate 80 (TW80), polyethylene glycol 15 hydroxystearate (HS 15) and polyoxyethylene castor oil (EL35) all have a good solubilizing effect on the aforementioned preparations.

A method for preparing the preferred reconstitution solvent includes the steps of: weighing a prescribed amount of surfactants, such as polysorbate 80, into a beaker, adding the prescribed amount of water, magnetic stirring until dissolved, filling with nitrogen into a vial according to the prescription amount to make the oxygen content in the headspace ≤7%, corking, capping, and moist heat sterilizing at 121° C.

It has been found through a large number of experiments that only 1.5-5 times weight of solubilizing solvent is needed to make the drug concentration at 1.5 mg/mL –15 mg/mL. It can be seen that although the surfactant is used for solubilization, the amount of surfactant used is greatly reduced due to the proper selection of the foregoing prescription.

For example, when the drug concentration was 1.7 mg/mL, the fold of polysorbate 80 (TW80), polyethylene glycol 15 hydroxystearate (HS 15), and polyoxyethylene castor oil (EL35) used were 3.9, 4.2 and 4.4, respectively. This indicates that the reconstitution effect of polysorbate 80 is slightly better than other reconstitution solvent. Therefore, polysorbate 80 is preferably the reconstitution solvent of docetaxel conjugate for injection in the present invention.

Example 7

The results of the stability retention test (accelerated retention test) of prescription 17 in Example 5 are as shown in Table 7.

TABLE 7

| Items | Range | Batch 1 | | Batch 2 | | Batch 3 | |
|---|---|---|---|---|---|---|---|
| | | 0 month | 25° C. 6 months | 0 month | 25° C. 6 months | 0 month | 25° C. 6 months |
| Character | White loose lumps | White loose lumps | No significant change | White loose lumps | No significant change | White loose lumps | No significant change |
| pH | 4.5~5.5 | Fit | Fit | Fit | Fit | Fit | Fit |
| Total impurity (%) | ≤3.0 | Fit | Increase 1.21 Fit | Fit | Increase 1.37 Fit | Fit | Increase 1.09 Fit |
| Content (%) | 90.0%~110.0% | Fit | Fit | Fit | Fit | Fit | Fit |

Specification: 25 mg; Packaging: Placement conditions for injection vials made of neutral borosilicate glass tubing: 25° C.±2° C., 60% RH±5% RH.

It can be seen from the above results that the drug is relatively stable under accelerated retention test conditions for 6 months and the impurities are within limits. The validity period is planned to be stored at 2-8° C. for 2 years.

Example 8 Pharmacodynamic Experiment (MDA-MB-231 Breast Cancer Cell Model)

MDA-MB-231 breast cancer cell model was used. One lyophilized powder injection of docetaxel conjugate IA1 (prescription 17 in Example 5, 25 mg specification) was used. Polysorbate 80 of Example 6 was used as the reconstitution solvent. The drug was diluted to 0.5 mg/ml with 5% glucose infusion. The experimental results are shown in the table below.

TABLE 8

Antitumor effect of docetaxel conjugate IA1 on MDA-MB-231 human breast cancer in mice.

| Group | Dose (mg/Kg) | Administration | Numbers of animals | Tumor weight inhibition (%) | P value |
|---|---|---|---|---|---|
| Saline control group | / | Iv. qw*2 | 5 | / | / |
| Lyophilized powder injection of docetaxel conjugate | 10 | Iv. qw*2 | 5 | 99 | <0.001 |

Figure 3:
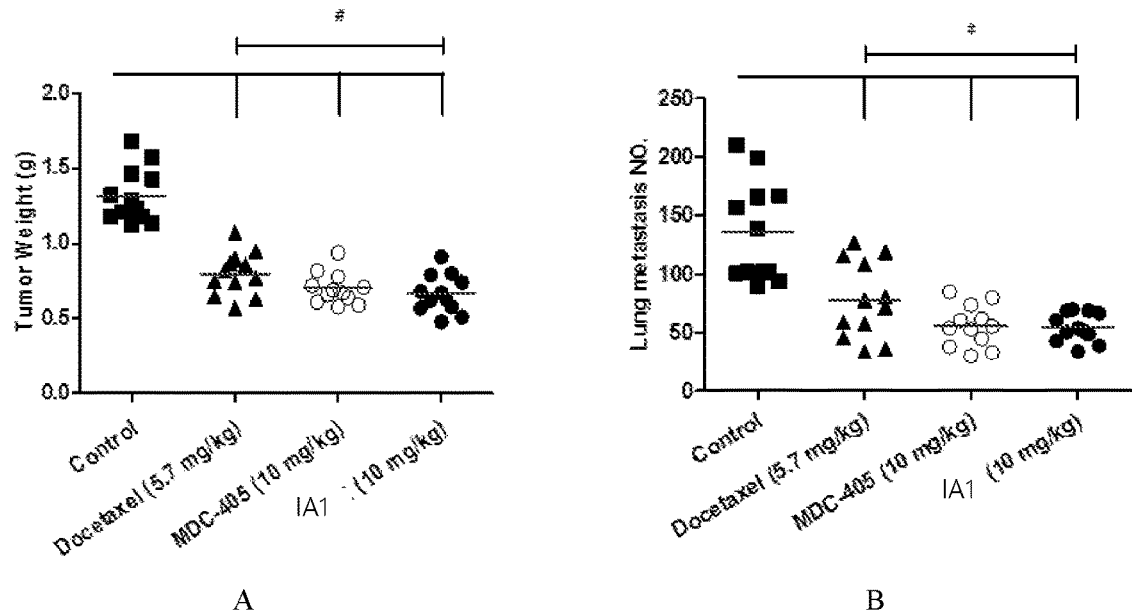
FIG. 3 shows the comparison results of the lung metastasis of 4T1 breast cancer in mice model treated with IA1 of the present patent, MDC-405 and docetaxel. Among them, 3A is the comparison result of breast tumor weight, and 3B is the comparison result of the number of metastatic nodules on the lung surface. 10 mg IA1 and 10 mg MDC-405 are equimolar with 5.7 mg docetaxel.

As shown in FIG. 3, in the MDA-MB-231 breast cancer cell model, the preparation has significant therapeutic effect compared to the control.

Example 9 Pharmacodynamic Experiment (4T1 Breast Cancer Cell Model)

A 4T1 breast cancer cell metastasis model of BALB/c mice was used. One lyophilized powder injection of docetaxel conjugate IA1 (prescription 17 in Example 5, 25 mg specification) was used. Polysorbate 80 of Example 6 was used as the reconstitution solvent. The drug was diluted to 0.5 mg/ml with 5% glucose infusion. The experimental results are shown in the table below.

TABLE 9

Antitumor effect of docetaxel conjugate IA1 on 4T1 breast cancer in mice model.

| Group | Dose (mg/Kg) | Administration | Numbers of animals |
|---|---|---|---|
| Saline control group | / | Iv. qw*4 | 5 |
| Lyophilized powder injection of docetaxel conjugate | 10 | Iv. qw*4 | 5 |

The results showed that in the 4T1 breast cancer cell model in mice, the tumor weight of breast cancer in the mice treated with docetaxel conjugate IA1 for injection was significantly smaller than that of the control group. The preparation has significant therapeutic effect compared to the control.

Example 10 Pharmacodynamic Experiment (Lung Metastasis of 4T1 Breast Cancer in BALB/c Mice)

A 4T1 breast cancer cell metastasis model in BALB/c mice was used. One lyophilized powder injection of docetaxel conjugate IA1 (prescription 17 in Example 5, 25 mg specification) was used. Polysorbate 80 of Example 6 was used as the reconstitution solvent. The drug was diluted to 0.5 mg/ml with 5% glucose infusion. Lung tissue was taken to count the number of nodules on the lung.

TABLE 10

Lyophilized powder injection of docetaxel conjugate IA1 inhibits lung metastasis of 4T1 breast cancer in BALB/c mice.

| | Control | lyophilized powder injection of docetaxel conjugate (10 mg/kg) |
|---|---|---|
| number of metastatic nodules on the lung (Mean ± SD) | 89 ± 5 | 49 ± 13 |
| Score (Mean ± SD) | 114 ± 10 | 58 ± 22 |

$p < 0.001$

TABLE 11

| I | II | III | IV |
|---|---|---|---|
| >5 mm | 3-5 mm | 1-2.9 mm | <1 mm |

Score = I × 4 + II × 3 + III × 2 + IV × I

The results showed that lyophilized powder injection of docetaxel conjugate IA1 significantly inhibited lung metastasis of 4T1 breast cancer in BALB/c mice.

In Vivo Activity Test Section.

Example 11 Using 4T1 Breast Cancer Lung Metastasis Model of Mice (1) Cell culture and tumor inoculation: 4T1 cells were cultured in 1640 medium (Gibco) containing 10% fetal bovine serum (Hyclone Corp, USA), 1% glutamine and 1% penicillin-streptomycin. The 4T1 cells in logarithmic growth phase were collected and the cell concentration was adjusted to $1.5 \times 10^6$/mL. 0.1 mL 4T1 cells ($1.5 \times 10^5$/per mouse) were inoculated in the fourth mammary fat pad of female BALB/c mice.

Grouping and administration: BALB/c mice were inoculated with 4T1 breast cancer cells in the mammary fat pad. The day of inoculation was DO. Mice were administered in groups on the fourth day after inoculation. The experiment consisted of four groups:
① solvent control group (blank control group),
② IA1 10 mg/kg group,
③ DTX (Docetaxel) 5.7 mg/kg group,
④ MDC 10 mg/kg group.
③ and ④ are positive control groups.

Each group had 10 animals. Mice were administered by tail vein injection once a week for 4 weeks. Animal weight and tumor volume were monitored during the administration. Animals were weighed every 2-3 days, and the long diameter and short diameter of breast tumors were measured with a vernier caliper. The tumor size was calculated by the formula: (½)×long diameter×(short diameter)². The experiment was terminated on the 28th day (D28). The mice were sacrificed by cervical dislocation after eyeball blood collection. The breast tumor and lung were weighed. The number of metastatic nodules on the lung surface was counted. The results of tumor weight are shown in FIG. 3A, and the results of the number of metastatic nodules on the lung surface are shown in FIG. 3B.

As shown in FIGS. 3A and 3B, IA1, MDC-405, and docetaxel significantly inhibited breast tumor weight and the number of metastatic nodules on the lung surface compared to the blank control group. More importantly, there is a significant difference in the inhibitory effects between IA1 and docetaxel in positive control group, while no significant difference in the inhibitory effect between MDC-405 and docetaxel was observed, suggesting that IA1 has a better inhibitory effect on tumor weight and cancer metastasis than MDC-405 and docetaxel.

(2) Cell culture and tumor inoculation: 4T1 cells were cultured in 1640 medium (Gibco) containing 10% fetal bovine serum (Hyclone Corp, USA), 1% glutamine and 1% penicillin-streptomycin. the 4T1 cells in logarithmic growth phase were collected and the cell concentration was adjusted to $1.5 \times 10^6$/mL. 0.1 mL 4T1 cells ($1.5 \times 10^5$/per mouse) were inoculated in the fourth mammary fat pad of female BALB/c mice.

Grouping and administration: BALB/c mice were inoculated with 4T1 breast cancer cells in the mammary fat pad. The day of inoculation was D0, and mice were administered in groups on the fourth day after inoculation. The experiment consisted of five groups:
① solvent control group (blank control group),
② IA1 10 mg/kg group,
③ DTX (Docetaxel) 5.7 mg/kg group,
④ DTX (5.7 mg/kg)+MDA-1 (4.53 mg/kg) group,
⑤ DTX (5.7 mg/kg)+MDA-1-linker (4.43 mg/kg) group.
③, ④ and ⑤ are positive control groups.

Each group had 10 animals. Mice were administered by tail vein injection once a week for 4 weeks. Animal weight and tumor volume were monitored during the administration. Animals were weighed every 2-3 days, and the long diameter and short diameter of breast tumors were measured with a vernier caliper. The tumor size was calculated by the formula: (½)×long diameter×(short diameter)$^2$. The experiment was terminated on the 28th day (D28). The mice were sacrificed by cervical dislocation after eyeball blood collection. The breast tumor and lung were weighed. The number of metastatic nodules on the lung surface was counted. The results of tumor weight are shown in FIG. 4A, and the results of the number of metastatic nodules on the lung surface are shown in FIG. 4B.

Figure 4:
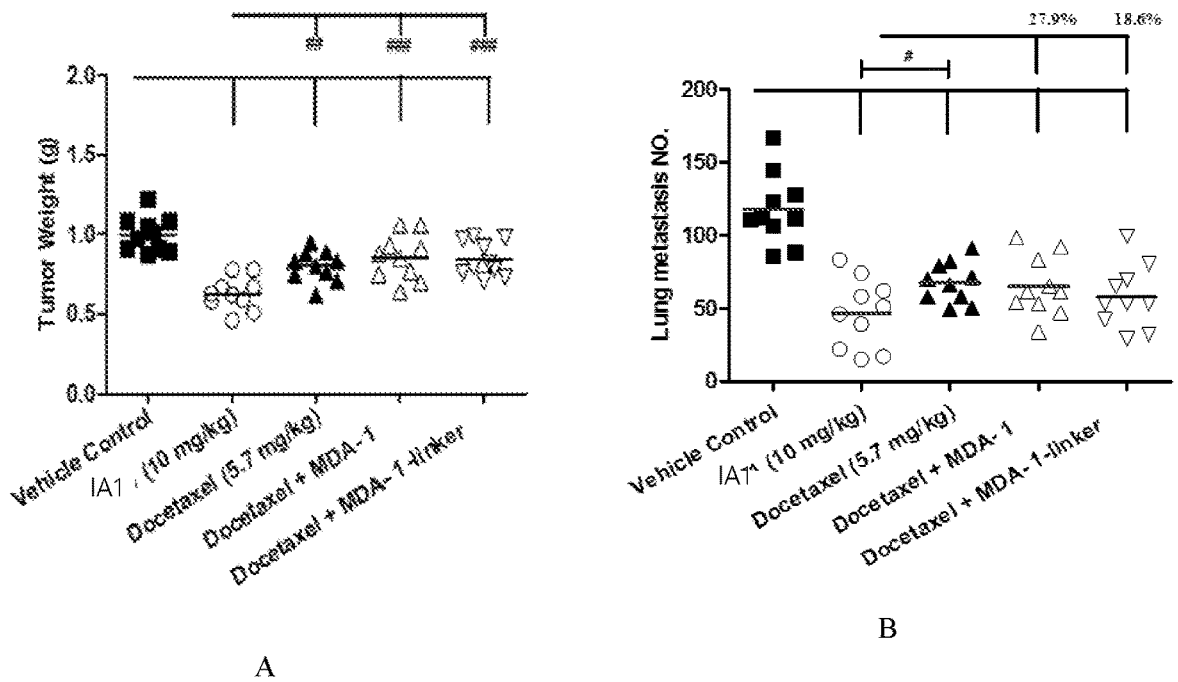
FIG. 4 shows the comparison results of the lung metastasis of 4A1 breast cancer in mice model treated with IA1 of the present patent, docetaxel, docetaxel plus MDA-1 and docetaxel plus MDA-1-linker. Among them, 4A is the comparison result of breast tumor weight, and 4B is the comparison result of the number of metastatic nodules on the lung surface. 10 mg IA1 is equimolar with 5.7 mg docetaxel.

As shown in FIG. 4A, IA1, docetaxel, docetaxel+MDA-1, and docetaxel+MDA-1-linker significantly inhibited the increase in breast tumor weight compared with the blank control group. More importantly, there is a significant difference in the inhibitory effects between IA1 and the positive control groups (docetaxel, docetaxel+MDA-1 and docetaxel+MDA-1-linker), indicating that IA1 has a better inhibitory effect on tumor than the positive control groups.

As shown in FIG. 4B, IA1, docetaxel, docetaxel+MDA-1, and docetaxel+MDA-1-linker significantly inhibited the increase in the number of metastatic nodules on the lung surface compared with the blank control group. More importantly, there is a significant difference in the inhibitory effects between IA1 and the positive control groups; compared with docetaxel+MDA-1 and docetaxel+MDA-1+linker, the inhibitory effects of IA1 increased by 27.9% and 18.6%, respectively. This suggests that IA1 has a better inhibitory effect on cancer metastasis than the positive control groups.

(3) Cell culture and tumor inoculation: 4T1 cells were cultured in 1640 medium (Gibco) containing 10% fetal bovine serum (Hyclone Corp, USA), 1% glutamine and 1% penicillin-streptomycin. The 4T1 cells in logarithmic growth phase were collected and the cell concentration was adjusted to $1.5 \times 10^6$/mL. 0.1 mL 4T1 cells ($1.5 \times 10^5$/per mouse) were inoculated in the fourth mammary fat pad of female BALB/c mice.

Grouping and administration: BALB/c mice were inoculated with 4T1 breast cancer cells in the mammary fat pad. The day of inoculation was D0, and mice were administered in groups on the fourth day after inoculation. The experiment consisted of six groups:
① solvent control group (blank control group),
② IA1 5 mg/kg group,
③ IA1 10 mg/kg group,
④ DTX (Docetaxel) 2.85 mg/kg group,
⑤ DTX (2.85 mg/kg)+MDA-1 (2.26 mg/kg) group,
⑥ DTX (2.85 mg/kg)+MDA-1-linker (2.21 mg/kg) group.
④, ⑤ and ⑥ are positive control groups.

Each group had 10 animals. Mice were administered by tail vein injection once a week for 4 weeks. Animal weight and tumor volume were monitored during the administration. Animals were weighed every 2-3 days, and the long diameter and short diameter of breast tumors were measured with a vernier caliper. The tumor size was calculated by the formula: (½)×long diameter×(short diameter)$^2$. The experiment was terminated on the 28th day (D28). The mice were sacrificed by cervical dislocation after eyeball blood collection. The breast tumor and lung were weighed. The number of metastatic nodules on the lung surface was counted. The results of tumor volume are shown in FIG. 5A, and the results of tumor weight are shown in FIG. 5B.

Figure 5:
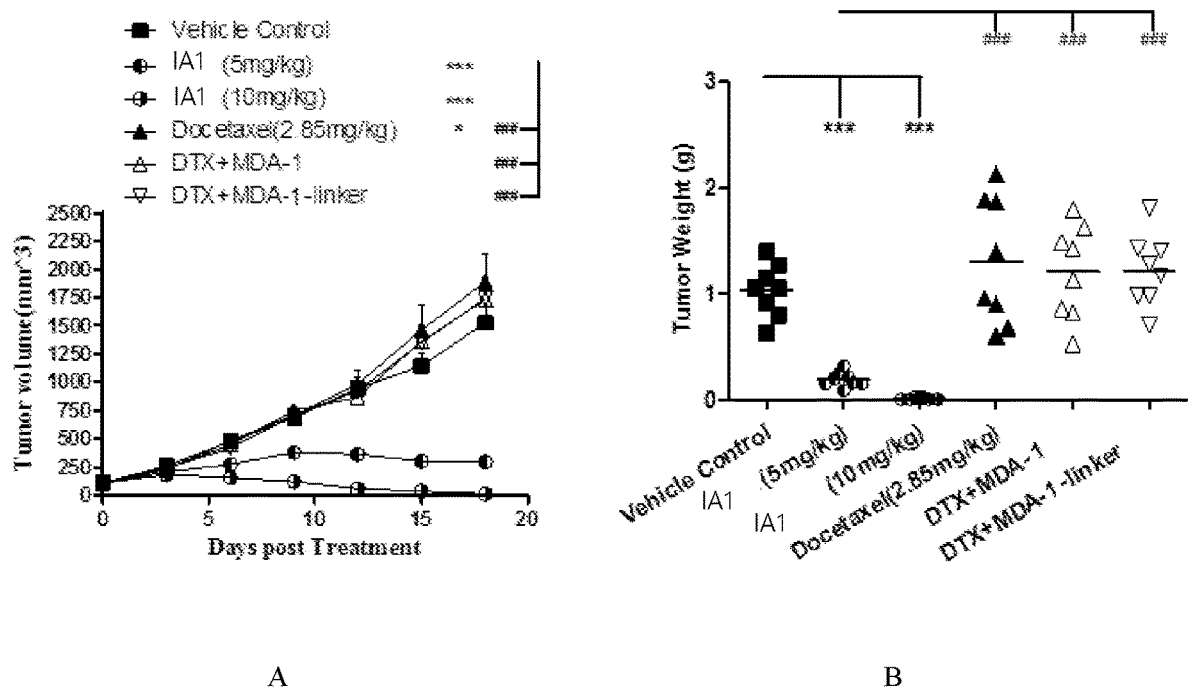
FIG. 5 shows the results of lung metastasis of 4T1 breast cancer in mice model treated with IA1, docetaxel, docetaxel plus MDA-1, and docetaxel plus MDA-1-linker. Among them, 5A is the comparison result of tumor volume, and 5B is the comparison result of tumor weight. DTX represents docetaxel. 5 mg IA1 is equimolar with 2.85 mg docetaxel.

As shown in FIGS. 5A and 5B, IA1, docetaxel, docetaxel+MDA-1, and docetaxel+MDA-1-linker significantly inhibited the increase in tumor volume and tumor weight compared with the blank control group. More importantly, there is a significant difference in the inhibitory effects between IA1 and the positive control groups (docetaxel, docetaxel+MDA-1, and docetaxel+MDA-1-linker), indicating that IA1 has a better inhibitory effect on tumor than the positive control groups.

Through the same experiment, it was found that other preferred compounds of the present invention have similar inhibitory effects on tumor and cancer metastasis with IA1, but IA1 is the most excellent. So, it can be inferred that the preferred compounds of the present invention have better inhibitory effects on tumor and tumor metastasis than MDC-405 and docetaxel.

Note. In the above experiments, the structure of MDA-1-linker is as follows:

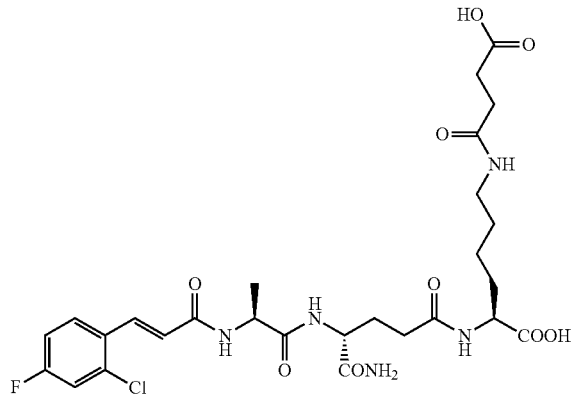 [SMILES: C[C@H](NC(=O)/C=C/c1ccc(F)cc1Cl)C(=O)N[C@H](CCC(=O)N[C@@H](CCCCNC(=O)CCC(=O)O)C(=O)O)C(N)=O]

The above embodiment is a preferred embodiment of the present invention, but the embodiment of the present invention is not limited by the above embodiment. Any other changes, modifications, substitutions, combinations, and simplifications are all equivalent replacement embodiments without deviating from the spirit and principle of the present invention, and all should be included in the protection scope of the present invention.

The invention claimed is:

1. A pharmaceutical composition, including: (1) a lyophilized powder of a docetaxel conjugate composition comprising (i) a docetaxel conjugate, and (ii) one or more pharmaceutically acceptable carriers which have no surfactant, and the pH value of the docetaxel conjugate composition ranges from 4.5-5.5 before lyophilization; and (2) a reconstitution solvent which contains one or more surfactants at 0.1 to 15 parts by weight, based on 1 part by weight of the docetaxel conjugate, wherein components (1) and (2) are separate in different chambers, and the docetaxel conjugate has the structure:
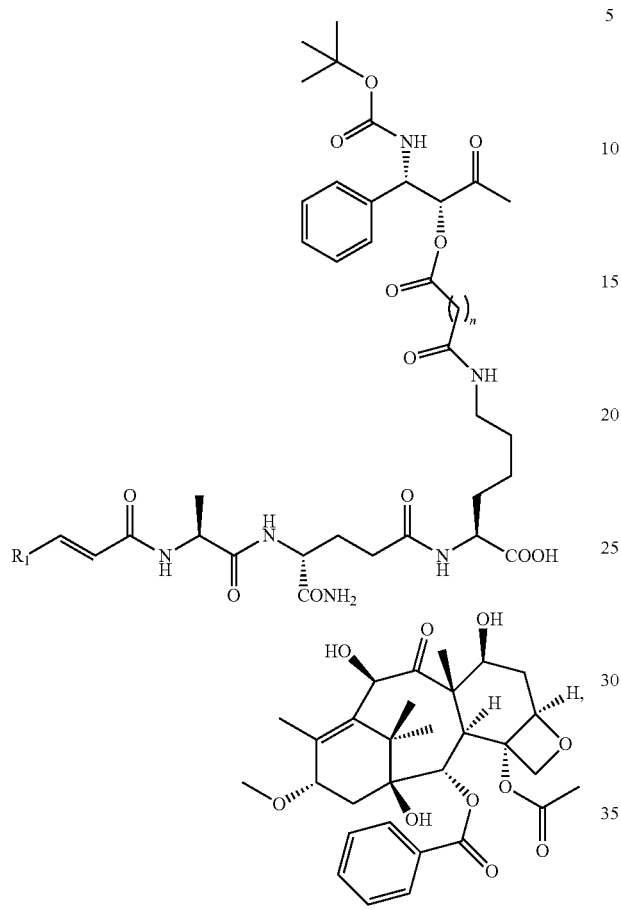
or a pharmaceutically acceptable salt thereof, or an ester thereof having the structure:
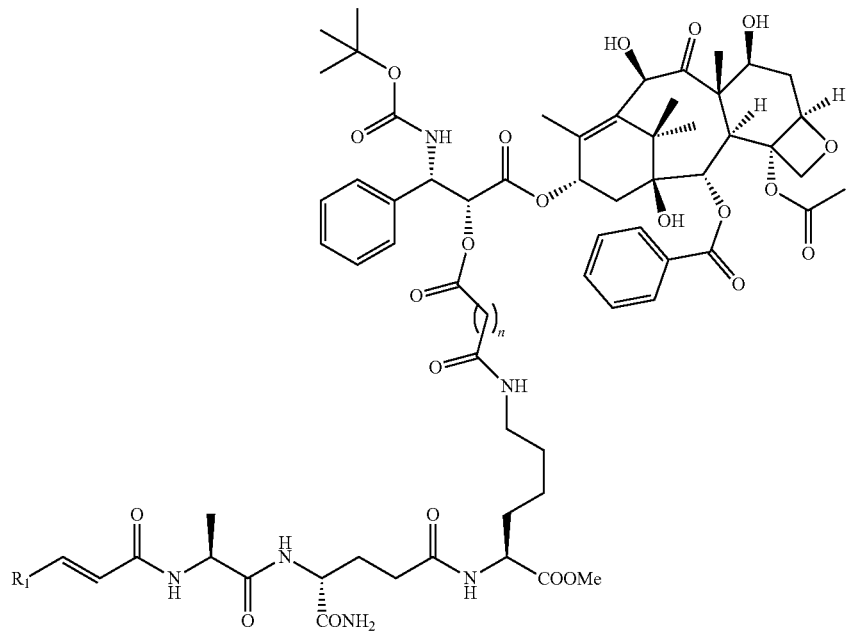

wherein, $R_1$ is selected from phenyl or one or more halogen-substituted phenyl, halogen is selected from fluorine, chlorine, bromine, or iodine, n is a natural number of 2 to 5, and is selected from 2, 3, 4, or 5.

2. The pharmaceutical composition according to claim 1, wherein the pharmaceutically acceptable carrier is selected from one or more fillers, the one or more fillers is 1 to 100 parts by weight based on 1 part by weight of the docetaxel conjugate, and the one or more fillers are one or more selected from the group consisting of mannitol, sucrose, glucose, trehalose, dextrose, lactose, hydroxyethyl starch, sulfobutyl-β-cyclodextrin, cyclodextrin, polyvinylpyrrolidone, histidine, valine, threonine, glycine, arginine, xylitol, sorbitol, fructose, poloxamer, gelatin, chitosan, sodium chloride, albumin, and any combination thereof.

3. The pharmaceutical composition according to claim 1 or 2, wherein the pharmaceutically acceptable carrier is selected from pH adjusting agents, and the pH adjusting agent is one or more selected from the group consisting of sodium hydroxide, potassium hydroxide, sodium dihydrogen phosphate, disodium hydrogen phosphate, potassium dihydrogen phosphate, dipotassium hydrogen phosphate, hydrochloric acid, citric acid, tartaric acid, acetic acid, malic acid, phosphoric acid, nitric acid, and sulfuric acid.

4. The pharmaceutical composition according to claim 1, wherein the one or more surfactants are at 3 to 10 parts by weight, based on 1 part by weight of the docetaxel conjugate.

5. The pharmaceutical composition according to claim 1, wherein the one or more surfactant in the reconstitution solvent are one or more selected from the group consisting of amphoteric surfactants and non-ionic surfactants, wherein the amphoteric surfactant is one or more selected from the group consisting of soya phospholipid, egg yolk phospholipid, phosphatidylcholine, phosphatidylethanolamine, serine phospholipid, inositol phospholipid, phosphatidic acid, cerebrolipid and hydrogenated phospholipid; the non-ionic surfactant is one or more selected from the group consisting of polysorbates, sorbitan esters, sucrose fatty acid esters, polyoxyethylene fatty acid esters, polyoxyethylene fatty alcohol ethers, and poloxamers.

6. The pharmaceutical composition according to claim 1, wherein the docetaxel conjugate is selected from the group consisting of:

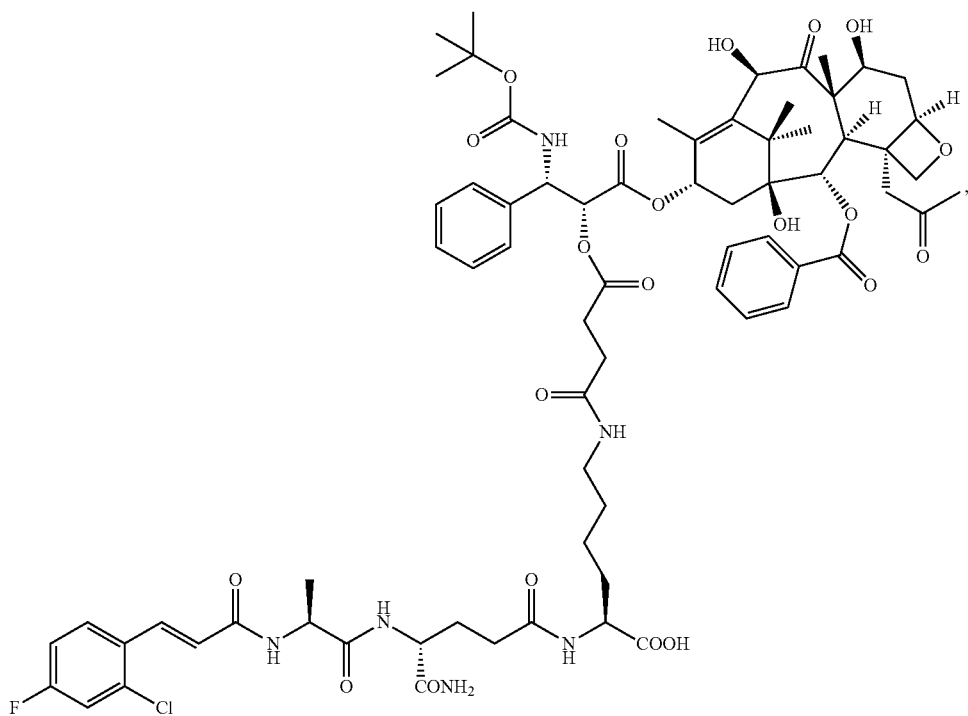

IA1

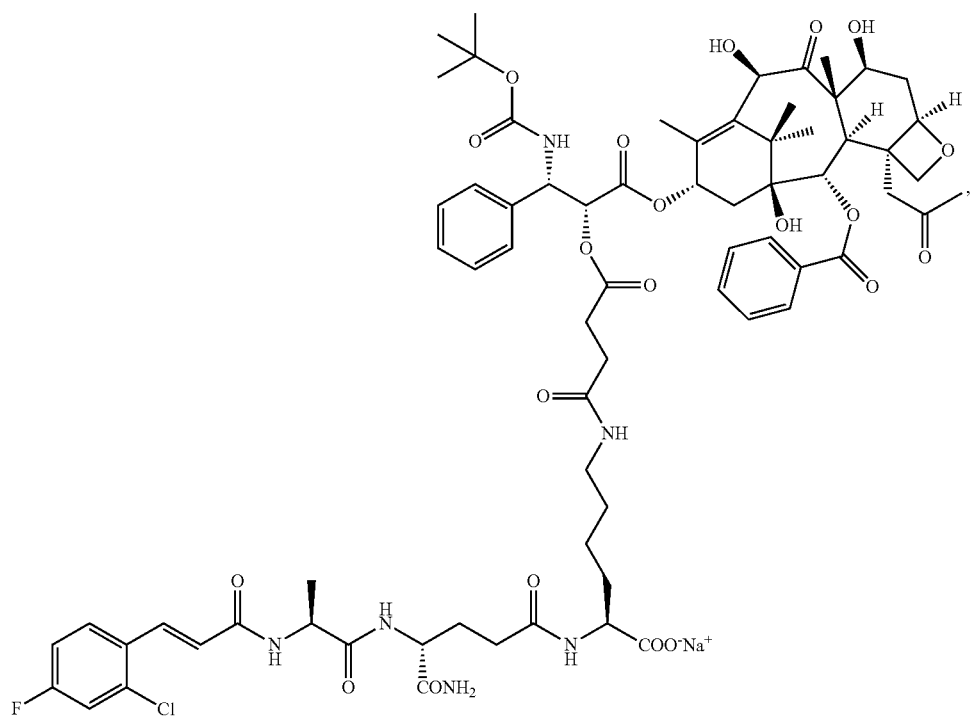
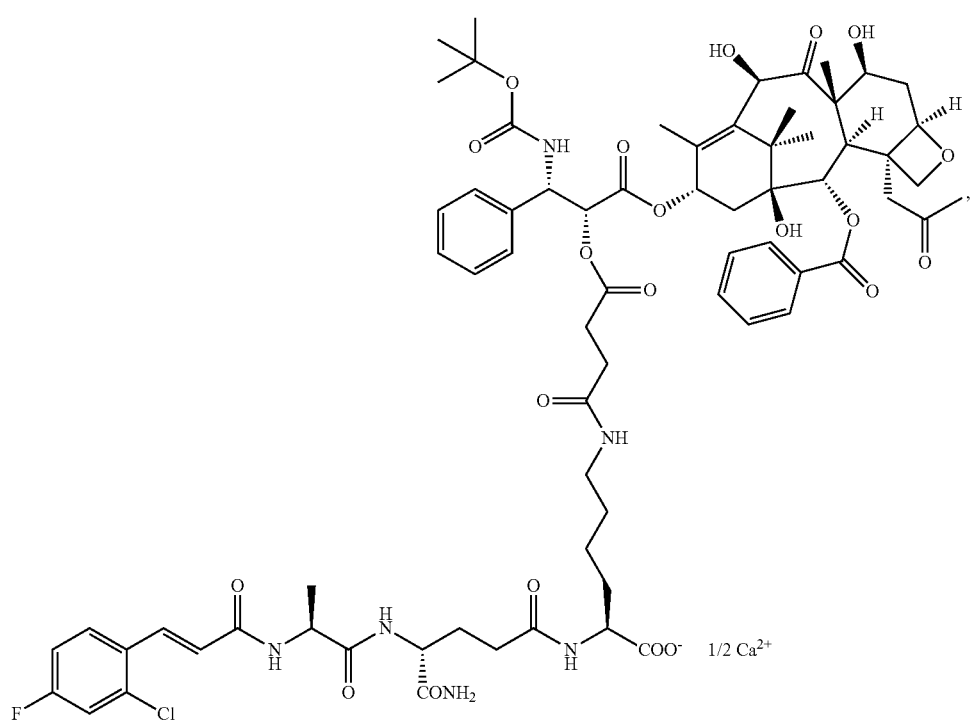

-continued
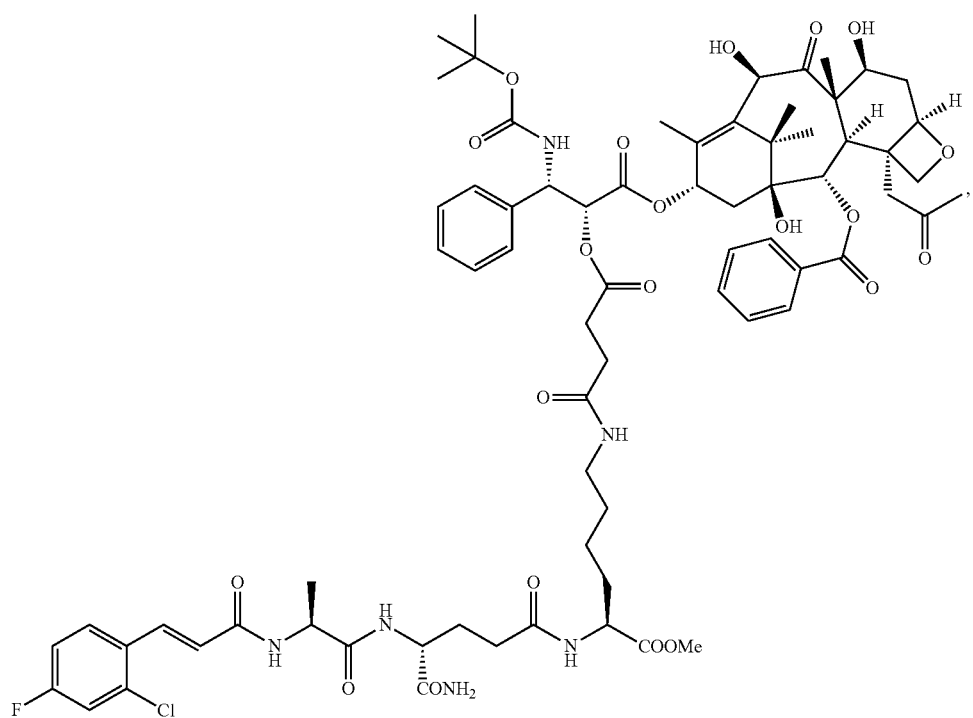
IA4
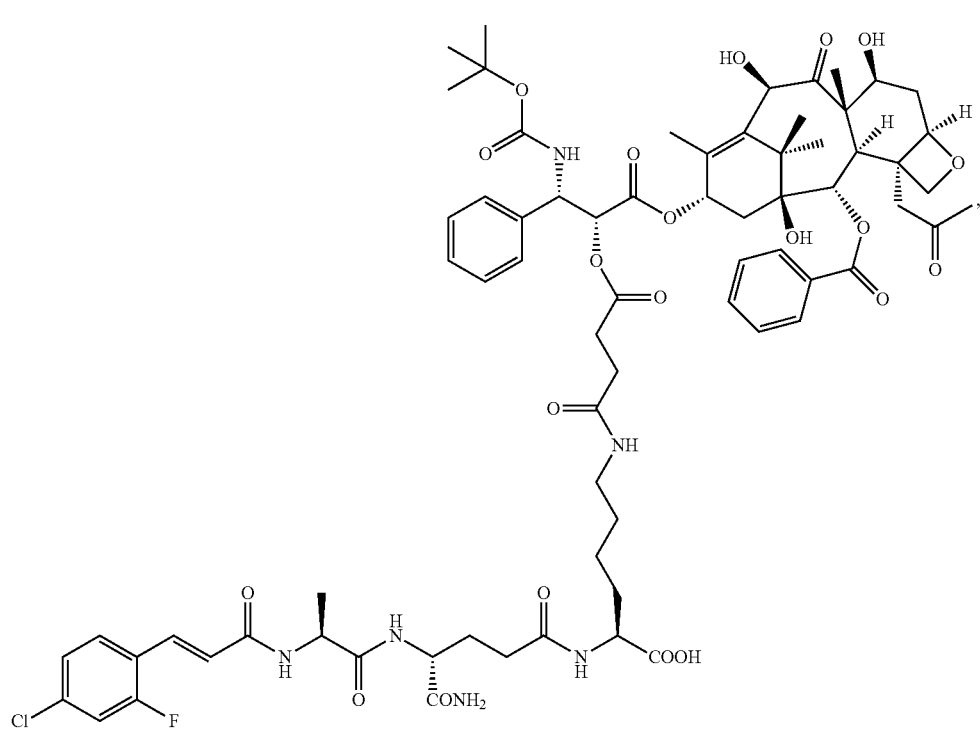
IA5

-continued
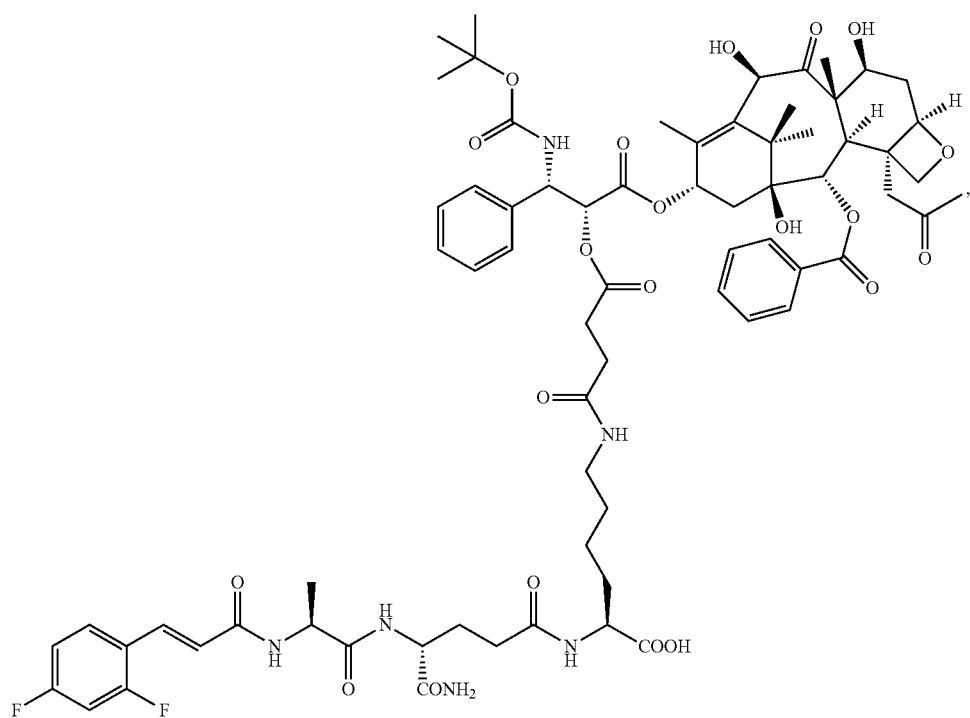
IA10
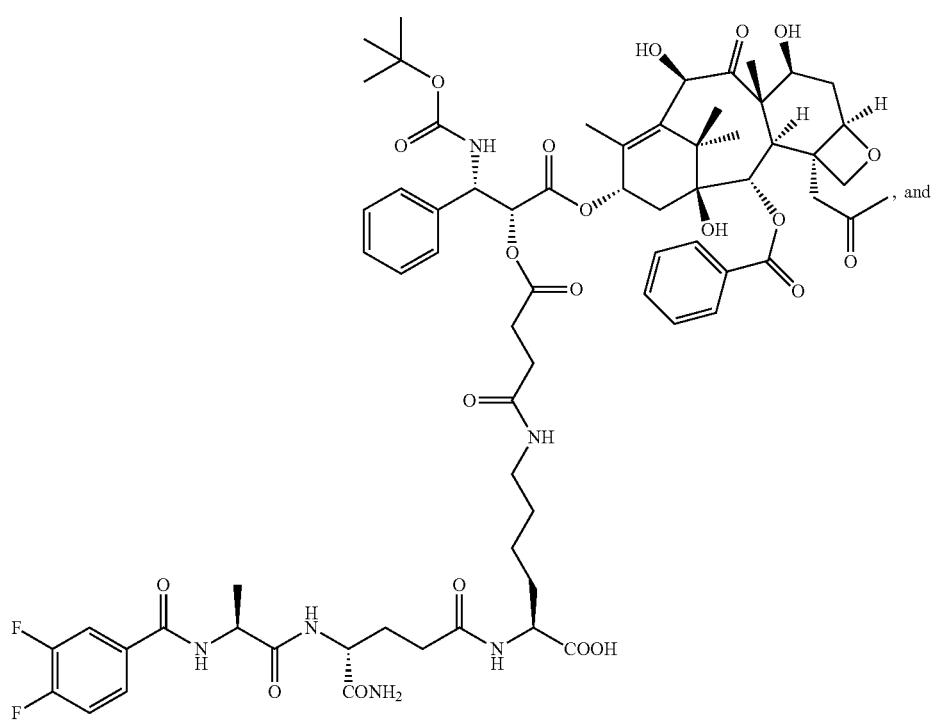
IA11

-continued

IA12

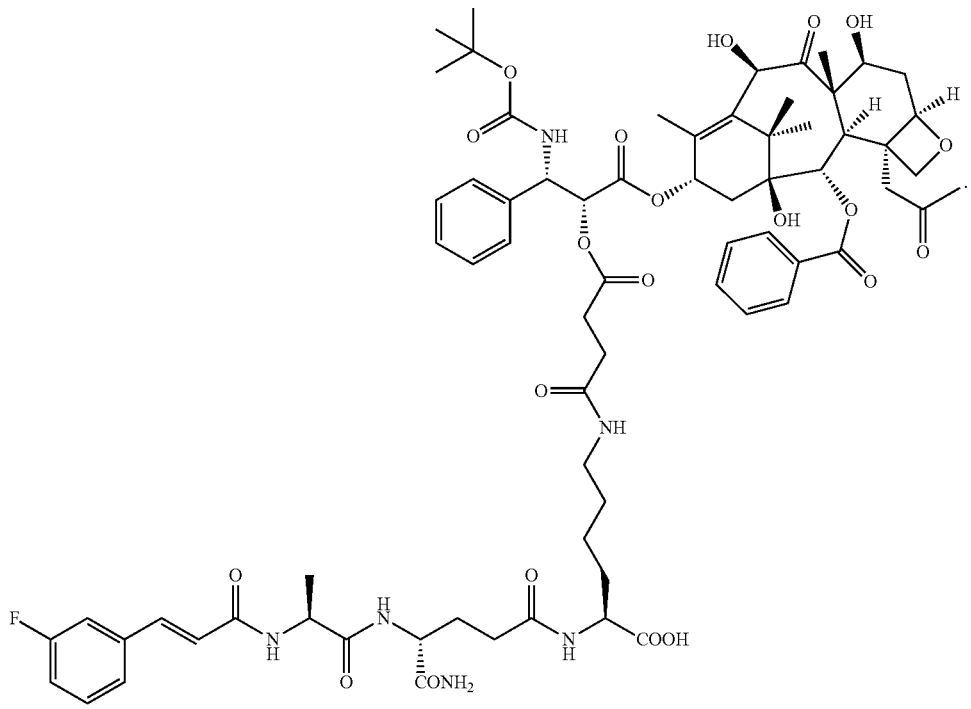

7. A method for preparing the lyophilized powder as defined in claim 1, wherein the method includes the steps of:
dissolving the docetaxel conjugate and one or more pharmaceutically acceptable carriers using a solvent;
adjusting the pH value to 4.5-5.5 to obtain the docetaxel conjugate composition; and
lyophilizing the docetaxel conjugate composition to remove the solvent.

8. The method according to claim 7, wherein the solvent is one or more selected from the group consisting of water, tert-butanol, ethanol, propylene glycol, polyethylene glycol, and cyclohexane.

9. The method according to claim 7, wherein the solvent is a combination of water and one or more of tert-butanol, ethanol, propylene glycol, and polyethylene glycol in a certain ratio.

10. The method according to claim 7, wherein the solvent is a mixed solvent of water and tert-butanol, with a weight ratio of 1:0.2 to 1:5.

11. The pharmaceutical composition according to claim 2, wherein the one or more fillers is 3 to 20 part by weight based on 1 part by weight of the docetaxel conjugate.

12. The pharmaceutical composition according to claim 3, wherein the pH adjusting agents are sodium dihydrogen phosphate and sodium hydroxide.

13. The pharmaceutical composition according to claim 1, wherein the one or more surfactants are selected from the group consisting of polysorbate-80, polyoxyl 35 castor oil, polyethylene glycol-15 stearate, and poloxamer 188.

* * * * *